United States Patent
Miller et al.

(10) Patent No.: US 8,596,145 B2
(45) Date of Patent: *Dec. 3, 2013

(54) SYSTEMS FOR DESIGNING A FOOT ORTHOTIC

(75) Inventors: J. Kevin Miller, Jackson, AL (US); Neal J. Beidleman, Aspen, CO (US); Michael A. Boennighausen, Los Altos, CA (US); Michael S. Latterman, Miami Beach, FL (US); Gregg E. Freebury, Lafayette, CO (US); Sue Ann Latterman, Mill Valley, CA (US); Huafeng Wen, Redwood City, CA (US)

(73) Assignee: Tensegrity Technologies, Inc., Mill Valley, CA (US)

(*) Notice: Subject to any disclaimer, the term of this patent is extended or adjusted under 35 U.S.C. 154(b) by 321 days.

This patent is subject to a terminal disclaimer.

(21) Appl. No.: 13/046,605

(22) Filed: Mar. 11, 2011

(65) Prior Publication Data
US 2011/0162238 A1 Jul. 7, 2011

Related U.S. Application Data

(63) Continuation of application No. 12/355,513, filed on Jan. 16, 2009, now Pat. No. 7,926,363.

(60) Provisional application No. 61/011,640, filed on Jan. 17, 2008, provisional application No. 61/038,020, filed on Mar. 19, 2008.

(51) Int. Cl.
*G01D 7/00* (2006.01)

(52) U.S. Cl.
USPC .................................................. 73/862.041

(58) Field of Classification Search
USPC ..................................................... 73/41–862
See application file for complete search history.

(56) References Cited

U.S. PATENT DOCUMENTS

| | | | |
|---|---|---|---|
| 3,826,145 A * | 7/1974 | McFarland | ..................... 600/595 |
| 4,449,264 A | 5/1984 | Schwartz | |
| 4,454,618 A | 6/1984 | Curchod | |
| 4,510,636 A | 4/1985 | Phillips | |
| 4,517,696 A | 5/1985 | Schartz | |

(Continued)

FOREIGN PATENT DOCUMENTS

| EP | 0820706 A2 | 1/1998 |
|---|---|---|
| WO | WO 93/25109 A1 | 12/1993 |

OTHER PUBLICATIONS

2002 Podiatric Practice Survey, Statistical Results, Al Fisher Associates, Inc., Journal of the American Podiatric Medical Association, vol. 93, No. 1, pp. 67-86 (2003).

(Continued)

*Primary Examiner* — Max Noori
(74) *Attorney, Agent, or Firm* — McDermott Will & Emery LLP; Judy M. Mohr

(57) ABSTRACT

Disclosed are methods and systems for design of a foot orthotic, and a foot orthotic device designed in accord therewith. More specifically described is an individualized foot orthotic device to correct and/or restore the ideal alignment and/or positioning of foot structures. In the method, sequential pressure is applied to regions on a plantar foot surface, and positional information is obtained about each region. Based on the positional information, an orthotic profile is determined, for design of one or more custom, individualized foot orthotic devices for a subject.

19 Claims, 20 Drawing Sheets

(56) References Cited

U.S. PATENT DOCUMENTS

| | | | |
|---|---|---|---|
| 4,774,954 A | 10/1988 | Ibrahim | |
| 4,778,717 A | 10/1988 | Fitchmun | |
| 4,876,758 A | 10/1989 | Rollof et al. | |
| 5,109,558 A * | 5/1992 | Di Blasi | 5/611 |
| 5,236,776 A | 8/1993 | Fitchmun et al. | |
| 5,312,669 A | 5/1994 | Bedard | |
| 5,336,459 A | 8/1994 | Barna | |
| 5,338,600 A | 8/1994 | Fitchmun et al. | |
| 5,354,604 A | 10/1994 | Blakeman et al. | |
| 5,390,430 A | 2/1995 | Fitchmun et al. | |
| 5,404,659 A | 4/1995 | Burke et al. | |
| 5,449,256 A | 9/1995 | Sundman | |
| 5,469,638 A | 11/1995 | Crawford, III | |
| 5,525,412 A | 6/1996 | Blakeman et al. | |
| 5,538,757 A | 7/1996 | Fitchmun et al. | |
| 5,571,607 A | 11/1996 | Blakeman et al. | |
| 5,581,912 A | 12/1996 | Adams | |
| 5,604,020 A | 2/1997 | Fitchmun | |
| 5,640,779 A | 6/1997 | Rollof et al. | |
| 5,689,446 A | 11/1997 | Sundman et al. | |
| 5,741,744 A | 4/1998 | Fitchmun | |
| 5,941,835 A * | 8/1999 | Sundman | 600/592 |
| 6,160,264 A | 12/2000 | Rebiere | |
| 6,205,230 B1 | 3/2001 | Sundman et al. | |
| 6,301,807 B1 | 10/2001 | Gardiner | |
| 6,430,831 B1 | 8/2002 | Sundman | |
| 6,493,958 B1 | 12/2002 | Tadin | |
| 6,625,897 B2 | 9/2003 | Tadin | |
| 6,654,705 B1 * | 11/2003 | Benson et al. | 702/168 |
| 6,864,687 B2 | 3/2005 | Walker et al. | |
| 6,904,692 B2 | 6/2005 | Tadin | |
| 6,976,322 B1 | 12/2005 | Walker | |
| 7,013,191 B2 | 3/2006 | Rubbert et al. | |
| 7,019,529 B2 | 3/2006 | Walker et al. | |
| 7,062,865 B1 | 6/2006 | Nordt, III | |
| 7,068,370 B2 | 6/2006 | Rosencwaig et al. | |
| D553,844 S | 10/2007 | Caine | |
| 7,287,293 B2 | 10/2007 | Cooke et al. | |
| 7,346,418 B2 | 3/2008 | Lowe | |
| 7,346,998 B2 | 3/2008 | Tadin et al. | |
| 7,367,074 B1 | 5/2008 | Bergquist | |
| D572,789 S | 7/2008 | Stites et al. | |
| 7,392,559 B2 | 7/2008 | Peterson | |
| 7,552,494 B2 | 6/2009 | Peterson | |
| 7,926,363 B2 * | 4/2011 | Miller et al. | 73/862.041 |
| 7,998,040 B2 * | 8/2011 | Kram et al. | 482/124 |
| 2005/0192677 A1 | 9/2005 | Ragnarsottir et al. | |
| 2005/0209535 A1 | 9/2005 | Dariush | |
| 2006/0213090 A1 | 9/2006 | Nole | |
| 2006/0270950 A1 | 11/2006 | Dariush | |
| 2006/0283243 A1 | 12/2006 | Petersen | |
| 2007/0073206 A1 | 3/2007 | Hatton et al. | |
| 2007/0112285 A1 | 5/2007 | Dar et al. | |
| 2007/0293798 A1 | 12/2007 | Hu et al. | |
| 2008/0208635 A1 | 8/2008 | Jung et al. | |
| 2008/0215162 A1 | 9/2008 | Farnsworth et al. | |
| 2008/0229612 A1 | 9/2008 | Sommer et al. | |

OTHER PUBLICATIONS

"Adult (Acquired) Flatfoot", The website of the American Academy of Orthopaedic Surgeons, 3 pages (2002).
Agarwal, "An in vitro study of cellular and molecular mechanisms of ligament scarring", Submitted to the Graduate Faculty of the School of Engineering in partial fulfillment of the requirements for the degree of Master of Science University of Pittsburgh 2004, 6 pages (2004).
"Age-Adjusted Rates of Foot Exam in the Last Year per 100 Adults with Diabetes", United States, 1994-2005, CDC, Atlanta, Ga. , 2 pages (2007).
Allaire et al., "Quantitative shape-function modeling of the forearm in medical imaging" Engineering in Medicine and Biology Society, Proceedings of the 25th Annual International Conference of the IEEE, 3. Issue, 17-21, vol. 3, pp. 2698-2701 (2003).
Alshami et al., "A review of plantar heel pain of neural origin: differential diagnosis and management" www.sciencedirect.com, doi:10.1016/j.math (2007).
Alvarez et al., "Stage I and II posterior tibial tendon dysfunction treated by a structured nonoperative management protocol: an orthosis and exercise program", Foot Ankle Int., vol. 27, No. 1, pp. 2-8 (2006) Abstract only.
American Physiological Society Science Blog, "Location of ulcerations in diabetic patients may be explained by blood flow", 5 pages (2003).
Amonoo-Kuofi et al., "Ligaments Related to the Intervertebral Canal and Foramen", The Clinical Anatomy & Management of Back Pain; vol. 1, pp. 114-117 (1977).
Andrews, Sharon, "The Effectiveness of Footwear, Orthoses and Casted Devices in Redistributing Plantar Pressure: A Systematic Review of the Literature", A Dissertation Submitted in Partial requirement for Bachelor of Science Degree in Podiatry, 104 pages (2004).
Anagnostakos et al., "Rupture of the anterior tibial tendon: three clinical cases, anatomical study, and literature review" Foot and Ankle International, vol. 27, No. 5, pp. 330-339 (2006).
Appleton, "Illustrations and mental imagery of archetypal forms of early organisms-a new approach to exposing and releasing habitual and dysfunctional posture", Journal of Bodywork and Movement Therapies, vol. 11, pp. 25-36 (2006).
Aquino et al., "Function of the windlass mechanism in excessively pronated feet" *Journal of American Podiatric Medical Association*, vol. 91, No. 5, pp. 245-250 (2001).
Arendt et al., "Stress injuries to bone in college athletes" The American Journal of Sports Medicine, vol. 31, pp. 959-968 (2003).
Aydin et al., "Proprioception of the ankle: a comparison between female teenaged gymnasts and controls" Foot and Ankle, vol. 23, No. 2, pp. 123-129 (2002).
Baker et al., "A randomized crossover trial of a wedged insole for treatment of knee osteoarthritis", Arthritis and Rheumatism. vol. 56, No. 4, pp. 1198-1203 (2007).
Ball et al., "Evolution of foot orthotics—part 1: coherent theory or coherent practice?", J Manipulative Physiol. Ther., vol. 25, No. 2, pp. 116-124 (2002) Abstract only.
Ball et al. "Evolution of foot orthotics—part 2: research reshapes long-standing theory", J. Manipulative Pysiol. Ther., vol. 25, pp. 125-134 (2002).
Baring, et al., "Management of rotator cuff disease: specific treatment for specific disorders", Best Practice & Research Clinical Rheumatology, vol. 21, No. 2, pp. 279-294 (2007).
Barwell et al., "four case study, the effect of the chiropractic adjustment on the brain wave pattern as measured by qeeg. summarizing an additional 100 (approximately) cases over a three year period", The World Chiropractic Alliance, 12 pages (2008).
Bass, "Father of aerobics pumps more iron", Ripped, 2 pages (2005).
Beach et al., "The contractile file-a new model of human movement" Journal of Body Movement Therapies, doi:10.1016/j.jbmt.2006.11. 008, pp. 1-10 (2007).
Bennell et al., "Effects of laterally wedged insoles on symptoms and disease progression in medial knee osteoarthritis: a protocol for a randomized, double-blind, placebo controlled trial", BMC Musculoskelet. Disord., vol. 8, No. 96, 13 pages (2007).
Berthalot et al., "Contribution of centralization phenomenon to the diagnosis, prognosis, and treatment of diskogenic low back pain" Joint Bone Spine, doi:10.1016/j.jbspin, pp. 1-5 (2007).
"Biomechanics of running: from faulty movement patterns come injuries" www.sportsinjurybulletin.com/archive/biomechanics-running.html, pp. 1-7 (Downloaded 2007).
Black, "Contact digitizing" Biomechanics, vol. 3, No. 4, pp. 59-60 (1996).
Blackwood et al., "The midtarsal joint locking mechanism" Foot and Ankle International, vol. 26, No. 12, pp. 1074-1080 (2005).
"BME/ME 456: Biomechanics, structure and function of ligaments and tendons", University of Michigan, http://www.engin.umich.edu/class/bme456/ligten/ligten.htm, 14 pages (2008).
"BME 332: Introduction to biosolid mechanics" www.engin.umich.edu/class/bme332/ch10ligten/bme332ligamenttendon.htm, 1-22 (2006).

(56) References Cited

OTHER PUBLICATIONS

Bojsen-Moller "Calcaneocuboid joint and stability of the longitudinal arch of the foot at high and low gear push off", Journal of Anatomy vol. 129, pp. 165-176 (1979).
Boulton et al., "Therapeutic Footwear in Diabetes, The good, the bad, and the ugly?", Diabetes Care, vol. 27, pp. 1832-1833 (2004).
Bramble et al., "Endurance running and the evolution of horno", Nature, vol. 432, pp. 345-352 (2004).
Brigham Young University News Release, "BYU student engineers invention to give customers 'happy feet' in 30 minutes or less", 2 pages, http://byunews.byu.edu/archive08-MAR-Capstone.aspx (2008).
Brown et al., "Measurement of dynamic pressures at the shoe-foot interface during normal walking with various foot orthoses using the FSCAN system", Foot Ankle Int. vol. 17, No. 3, pp. 152-156 (1996) Abstract only.
Burns et al., "Effective orthotic therapy for the painful cavus foot: a randomized controlled trial", Journal of the Podiatric Medical Association, vol. 96, No. 3, pp. 205-211 (2006).
Carragee, "Persistent low back pain" New England Journal of Medicine, vol. 352, pp. 1891-1898 (2005).
Caselli and Longobardi "Lower extremity injuries at the new york city marathon" Journal of the American Podiatric Medical Association, vol. 87, No. 1, pp. 34-37 (1997).
Chen and Ingber, "Tensegrity and mechanoregulation: from skeleton to cytoskeleton", Osteoarthritis and Cartilage, vol. 7, pp. 81-94 (1999).
Christensen, "Plastic deformation and long-term support", Dynamic Chiropractic, vol. 17, No. 26, 3 pages (1999).
Chuter et al., "Variability of neutral-position casting of the foot", Journal of the American Pediatric Medical Association, vol. 93, No. 1, pp. 1-5 (2003).
Cibulka et al., "Unilateral hip rotation range of motion asymmetry in patients with sacroillac joint regional pain" White Paper-Michael Cibulka Jefferson County Rehabilitation & Sports Clinic, 430 Truman blvd., Crystal City, MO 63019, 11 pages (2002).
Cipra, "Catching fly balls: a new model steps up to the plate", Science, vol. 268, pp. 28 (1995).
Claeys, "The analysis of ground reaction forces in pathological gait secondary to disorders of the foot" International Orthopaedics (SICOT) vol. 7, pp. 113-119 (1983).
Claisse et al., "Effect of orthotic therapy on claw toe loading. results of significance testing at pressure sensor units", Journal of the American Podiatric Medical Association, vol. 94, No. 3, pp. 246-254 (2004).
Cornwall et al., "Reliability and validity of clinically assessing first-ray mobility of the foot", Journal of the American Podiatric Medical Association, vol. 94, No. 5, pp. 470-476 (2004).
Cornwall and McPoil, "The effect of foot orthotics on the initiation of plantar surface loading",. Clin. Biomech., vol. 12, No. 3, pp. S4 (1997) Abstract only.
Costa and Dyson, "The integration of acetic acid iontophoresis, orthotic therapy and physical rehabilitation for chronic plantar fasciitis: a case", J. Can. Chiropr. Assoc., vol. 51, No. 3, pp. 166-174 (2007).
Crelin, "The development of the human foot as a resume if its evolution", Foot & Ankle International, vol. 3, No. 6, pp. 305-321 (1993).
Crock, "Internal disc disruption" www.chirogeek.com/003 IDD-Tutorial.htm, 14 pages (2003).
Cullen et al., "Diagnostic accuracy of shoulder ultrasound performed by a single operator", Australas, Radiol., vol. 51, No. 3, pp. 226-229 (2007) Abstract only.
Curran and Dananberg, "Future of gait analysis-a podiatric medical perspective" Journal of American Podiatric Medical Association, vol. 95, No. 2, pp. 1340-1342 (2005).
Cuthbert and Goodheart, "On the reliability and validity of manual muscle testing: a literature Review" Chiropractic & Osteopathy, vol. 15, No. 4, pp. 1-30 (2007).
Dalton, "Overuse injuries in adolescent athletes", Sports Medicine, vol. 13, No. 1, pp. 58-70 (1982).

D'Ambrosia, "Orthotic devices in running injuries" Clinics in Sports Medicine, vol. 4, No. 4, pp. 611-618 (1985).
Dananberg and Guiliano, "Chronic low-back pain and its response to custom-made foot orthoses", Journal Am. Podiatr. Med. Assoc., vol. 89, No. 3, pp. 109-117 (1999).
Dananberg, "Sagittal plane biomechanics", Journal of American Podiatric Medical Association, vol. 90, No. 1, pp. 47-50 (2000).
Dananberg, "Lower back pain as a gait-related repetitive motion injury" Journal of the American Podiatric Medical Association vol. 76, No. 11, pp. 253-267 (1997).
D'Aout et al., "Locomotion in bonobos (pan paniscus): differences and similarities between bipedal and quadrupedal terrestrial walking, and a comparison with other locomotor modes" Journal of Anatomy, vol. 204, pp. 353-361 (2004).
Davies and Saxby, "Intercuneiform instability and the "Gap"sign", Foot and Ankle International, vol. 20, No. 9, pp. 606-609 (1999).
De Asla, and Deland, "Anatomy and biomechanics of the foot and ankle" Foot and Ankle: Orthopedic Surgery Essentials, By David B. Thordarson, Paul Tornetta; Thomas A Einhorn Contributor David B, Thordarson, Lippincott Williams & Wilkins, Chapter 1, pp. 1-23 (2004).
Devine, "The versatility of human locomotion" American Anthropologist, vol. 87, pp. 560-568 (1985).
De Wit et al., "Biomechanical analysis of the stance phase during barefoot and shod running", Journal of Biomechanics, vol. 33, pp. 269-278 (2000).
Deyo and Weinstein, "Low back pain" New England Journal of Medicine, vol. 344, No. 5, pp. 363-370 (2001).
Dowling et al., "Does obesity influence foot structure and plantar pressure patterns in prepubescent children?", International Journal of Obesity, vol. 25, pp. 845-852 (2001).
Dowling et al., "What are the effects of obesity in children on plantar pressure distributions?", International Journal of Obesity, vol. 28, pp. 1514-1519 (2004) Abstract only.
Duffin et al., High plantar pressure and callus in diabetic adolescents, incidence and treatment, Journal of the American Podiatric Medical Association, vol. 93, No. 3, pp. 214-220 (2003).
Dwyer et al., "Blockade of the sympathetic nervous system degrades ligament in a rat MCL model", Journal of Applied Physiology, vol. 96, pp. 711-718 (2004).
Dyck et al., "Endurance training increases FFA oxidation and reduces triacylglycerol utilization in contracting rat soleus" American Journal of Physiological Endocrinal Metab., vol. 278, No. 5, pp. E778-E785 (2000).
Ebersole, "Mechanomyography takes a sound approach to muscle function" Biomechanics, vol. 19, No. 12, pp. 53-59 (2002).
Elftman, "The transverse tarsal joint and its control", Clin. Orthop., vol. 16, pp. 41-46 (1960).
Elftman and Manter, "The evolution of the human foot, with special reference to the joints" Journal of Anatomy, vol. 70, No. 1, pp. 56-67 (1935).
Ellegaard et al., "Ultrasound in finger joints: findings in normal subjects and pitfalls in the diagnosis of synovial disease", Ultraschall Med., vol. 28, No. 4, pp. 401-408 (2007) Abstract only.
Ferri et al., "Weight bearing CT scan of severe flexible pes planus deformities", Foot & Ankle International, vol. 29, No. 2, pp. 199-204 (2008).
Filippucci et al., "Ultrasound imaging for the rheumatologist VII. Ultrasound imaging in rheumatoid arthritis", Clin Exp Rheumatol., vol. 25, No. 1, pp. 5-10 (2007) Abstract only.
Finestone et al., "A prospective study of the effect of foot orthoses composition and fabrication on comfort and the incidence of overuse injuries", Foot Ankle Int., vol. 25, No. 7, pp. 462-466 (2004).
Folman et al., "Attenuation of spinal transients at heel strike using viscoelastic heel insoles: an in vivo study", Prev. Med., vol. 39, No. 2, pp. 351-354 (2004) Abstract only.
Frey and Zamora, The effects of obesity on orthopaedic foot and ankle pathology. Foot Ankle Int. vol. 28, No. 9, pp. 996-999 (2007) Abstract only.
Fritsch and Haslbeck "Significance of pedography in the diagnosis and treatment of the diabetic foot syndrome", MMW Fortschr. Med., vol. 146, No. 26 pp. 51-54 (2004) Abstract only.

(56) References Cited

OTHER PUBLICATIONS

Frykberg et al., "Diabetic Foot Disorders: A Clinical Practice Guideline", 2006 Revision, J. of Foot and Ankle Surgery, vol. 45, No. 5, Supplement to issue, pp. 1-68 (2006).
Fuhr and Menke, "Status of activator methods chiropractic technique, theory, and practice" Journal of Manipulative and Physiological Therapeutics, vol. 28, No. 2, pp. 1-36(2005).
Fuller, "Center of pressure and its theoretical relationship to foot pathology" Journal of the American Podiatric Medical Association, vol. 89, No. 6, pp. 278-291 (1999).
Fuller, "A new approach to biomechanics and orthotic therapy" Podiatry Management, pp. 127-135 (2003).
Fuller, "Reinventing biomechanics", Podiatry Today, vol. 13, No. 3, pp. 1-7 (2000).
Fuller, Buckminster, "Tensegrity" www.rwgrayprojects.com/rbfnotes/fpapers/tensegrity/tenseg01.html, pp. 1-22 (2007).
"Further Evidence Against the Claims of Fruitarian Evolution" www.beyondveg.com/billings-t/comp-anat-4d.shtml. pp. 1-5 (2006).
Galli et al., "Life on the wire: on tensegrity and force balance in cells", Acta Bio. Med., vol. 76, pp. 5-12 (2005).
Gayle et al., "Effect of therapeutic footwear on foot reulceration in patients with diabetes: a randomized controlled trial", JAMA, vol. 287, pp. 2552-2558 (2002).
Gebo, "Climbing, brachiation and terrestrial quadrupedalism: historical precursors of hominid bipedalism", American Journal of Physical Anthropology, vol. 101, pp. 55-92 (1996).
Gefen et al., "Biomechanical analysis of the three-dimensional foot structure during gait: a basic tool for clinical application", Journal of Biomechanical Engineering, vol. 122, pp. 630-639 (2000).
Gheluwe and Dananberg, "Changes in plantar foor pressure with in-shoe varus or valgus wedging", Journal of the American Podiatric Medical Association, vol. 94, No. 1, pp. 1-11 (2004).
Glascoe et al., "Anatomy and biomechanics of the first ray", Physical Therapy, vol. 79, No. 9, pp. 854-859 (1999).
Glaser. Edward et al., "Focus on function in custom foot orthotics", California Podiatric Medical Association, pp. 19-23 (2007).
Glaser et al., "Theory, practice combine for custom orthoses", BioMechanics Archives, 4 pages (2006).
Glasoe and Saltzman, "Case report: recalcitrant posterior tibialis tendinitis from an unstable first ray", Foot and Ankle Surgery, vol. 8, pp. 281-284 (2002).
Gracovetsky, "Linking the spinal engine with the legs: a theory of human gait" Evolution & Gait, vol. 20, pp. 243-251 (1999).
Gracovetsky, "Analysis and interpretation of gait in relation to lumbo pelvic function", 4th Interdisciplinary World Congress on Low Back & Pelvic Pain, pp. 45-63 (2001).
Gracovetsky, "The role of the upper extremities in the control of the lumbar pelvic and cervical spine motion during gait" Veldhoven, 1 page, (2002).
Gravate et al., "Plantar pressure distribution analysis in normal weight young women and men with normal and claw feet" Clinical Anatomy, vol. 18, No. 4, pp. 245-250 (2005).
Green et al., "Diabetic foot: evaluation and management", South Med. J., vol. 95, No. 1, pp. 95-101 (2002).
Grieve, "The defeat of gravity in weightlifting" British Journal of Sports Medicine, vol. 5, pp. 37-41 (1970).
Groner, "Orthoses symbiosis: clinicians are finding a middle ground in the debate over custom versus prefab foot orthoses", Biomechanics, vol. 22, No. 5, pp. 22-33 (2005).
Gross et al., "The impact of custom semirigid foot orthotics on pain and disability for individuals with plantar fasciitis", J. Orthop. Sports Phys. Ther., vol. 32, No. 4, pp. 149-157 (2002) Abstract only.
Grumbine, "Computer-generated orthoses. A review", Clin. Podiatr. Med. Surg., vol. 10, No. 3, pp. 377-391 (1993) Abstract only.
Guidemond et al., "The effects of insole configurations on forefoot plantar pressure and walking convenience in diabetic patients with neuropathic feet", Clin. Biomech., vol. 22, No. 1, pp. 81-87 (2006) Abstract only.

Guldemond et al., "Comparison of foot orthoses made by podiatrists, pedorthists and orthotists regarding plantar pressure reduction in The Netherlands", BMC Musculoskelet. Disorders, vol. 6, pp. 61, 11 pages (2005).
Guldemond et al., "Casting methods and plantar pressure. effects of custom-made foot orthoses on dynamic plantar pressure distribution", Journal of the American Podiatric Medical Association, vol. 96, No. 1, pp. 9-18 (2006).
Guo et al. "Back pain prevalence in US industry and estimates of lost workdays", Am. J. Public Helath, vol. 89, No. 7, pp. 1029-1035 (1999).
Gurney, "Leg length discrepancy", Gait and Posture, vol. 15, pp. 195-206 (2002).
Haake et al., "Extracorporeal shock wave therapy for plantar fasciitis: randomised controlled multicentre trail", BMJ, vol. 327, No. 7406, 8 pages (2003).
Harcourt-Smith, "Fossils, feet and the evolution of human bipedal locomotion", Journal of Anatomy, vol. 204, pp. 403-416 (2004).
Harris et al., "Diagnosis and treatment of pediatric flatfoot", The Journal of Foot and Ankle Surgery, vol. 43, No. 6, pp. 341-370 (2004).
Harwood et al., "A lisfranc fracture-dislocation in a football player" The Journal of the American Board of Family Practice, vol. 16, pp. 69-72 (2003).
Hawks, "The hominid pelvis", http://johnhawks.net/weblog/topics/bipedalism/bipedal_pelvis.html, pp. 1-8 (2005).
Hicks, "The mechanics of the foot-I. the joints" Journal of the Anatomy, vol. 8, No. 1, pp. 345-357 (1954).
Hicks, "The mechanics of the foot-II the plantar aponeurosis and the arch" Journal of Anatomy, vol. 8, No. 1, pp. 25-30 (1953).
Hicks, "The mechanics of the foot" Journal of the Anatomy, vol. 88, No. 1, pp. 25-30 (1954).
Hickson, et al., "Skeletal muscle enzyme alterations after sprint and endurance training" Journal of Applied Physiology, vol. 40, No. 6, pp. 868-872 (1975).
"History of foot ulcer among persons with diabetes", United States, 2000-2002. MMWR Weekly, vol. 52, No. 45, pp. 1098-1102 (2003).
Hockenbury, "Acquired flatfoot", E-Medicine, Online article, 18 pages (2005).
Hodgson, "The effect of 2 different custom-molded corrective orthotics on plantar pressure" Journal of Sports Rehabilitation, vol. 15, pp. 33-44 (2006).
Hughes, "The art of running: a biomechanical look at efficiency", www.texastrack.com/coaching_article 5.htm, pp. 1-4 (2007).
Hunt et al., "Inter-segment foot motion and ground reaction forces over the stance phase of walking", Clinical Biomechanics, vol. 16, pp. 592-600 (2001).
Hyer et al., "The incidence of the intermetatarsal facet of the first metatarsal and its relationship to metatarsus primus varus: a cadaveric study" Journal of Foot and Ankle Surgery, vol. 44, No. 3, pp. 200-202 (2005).
Ingber, "Tensegrity I. cell structure and hierachical systems biology" Journal of Cell Science, vol. 116, pp. 1157-1173 (2003).
Ingber, "Tensegrity II. how structural networks influence cellular information processing networks" Journal of Cell Science, vol. 116, pp. 1397-1408 (2003).
Ingber, "Tensegrity: the architectural basis of cellular mechanotransduction", Annual Review of Physiology, vol. 59, pp. 575-599 (1997).
International Search Report and Written opinion from related PCT Patent Application No. PCT/US2009/000298 mailed May 7, 2009, 13 pages.
Janisse and Janisse, Pedorthic and orthotic management of the diabetic foot, Foot Ankle Clin., vol. 11, No. 4, pp. 717-734 (2006) Abstract only.
Jennings, "Factors associated with running injuries" www.podiatry.curtin.edu.au/encyclopedia/running/content.html, pp. 1-8 (2005).
Johanson et al., "Effects of three different posting methods on controlling abnormal subtalar pronation", Phys Ther., vol. 74, No. 2, pp. 149-158, discussion 158-61. (1993) Abstract only.
Jones and MacFarlane, "Epidemiology of low back pain in children arid adolescents" ADC BMJ Journal, vol. 90, pp. 312-316 (2005).

(56) References Cited

OTHER PUBLICATIONS

Jones, "The human foot. an experimental study of its mechanics, and the role of its muscles and ligaments in the support of the arch" American Journal of Anatomy, vol. 68, No. 1, pp. 1-40 (1941).
Kang et al., "Correlations between subjective treatment responses and plantar pressure parameters of metatarsal pad treatment in metatarsalgia patients: a prospective study", BMC Musculoskelet. Disorders, vol. 7, 9 pages (2006).
Karas et al., "Compensatory midfoot dorsiflexion in the individual with heelcord tightness: implications for orthotic device designs", Journal of Prosthetics and Orthotics, vol. 14, No. 2, pp. 81-91 (2002).
Karchin, "Biomaterials tutorial" www.uweb.engr.washington.edu/research/tutorials/mechproperties.html, pp. 1-5 (2006).
Kato et al., "The reduction and redistribution of plantar pressures using foot orthoses in diabetic patients", Diabetes Res Clin Pract., vol. 31, No. 1-3, pp. 115-118 (1996) Abstract only.
Kelly, "Tripedal knuckle-walking: a proposal for the evolution of human locomotion and handedness" Journal of Theoretical Biology, vol. 213, pp. 333-358 (2001).
Kelly, "Podiatric and clinical biomechanics" www.podiatry.co.uk/articles/podiatric.html, pp. 1-12 (2007).
Kidd, "Evolution of the rearfoot", Journal of the American Podiatric Medical Association, vol. 89, No. 1, pp. 2-17 (1999).
Kirby, "Subtalar joint axis location and rotational equilibrium theory of foot function", American Journal of Podiatric Medicine, vol. 91, No. 9, pp. 465-487 (2001).
Kline, "Historical review: surgical release of the first branch of the lateral plantar nerve for chronic heel pain", Ankle Int., vol. 23, No. 3, pp. 208-211 (2002).
Koh et al., "Ultrasonographic examination of the synovial fold of the radiohumeral joint", J Shoulder Elbow Surg., vol. 16, No. 5, pp. 609-615 (2007) Abstract only.
Kohls-Gatzoulis et al., "Tibialis posterior dysfunction: a common and treatable cause of adult acquired flatfoot", BMJ, vol. 329, pp. 1328-1333 (2004).
Konrad, "The ABC of EMG" www.noraxon.com/emg/index.php3, pp. 1-60 (2005).
Kryzak and Degroot "Adult onset flatfoot associated with an intramuscular hemangioma of the posterior tibialis muscle", Orthopedics, vol. 31, No. 280, 4 pages (2008).
Kuhn et al., "Radiographic evalution of weight-bearing orthotics and their effect on flexible pes planus", Journal of Manipulative and Physiological Therapeutics, vol. 22, No. 4, pp. 221-226 (1999).
Kulcu et al., "Immediate effects of silicone insoles on gait pattern in patients with flexible flatfoot", Foot & Ankle International, vol. 28, No. 10, pp. 1053-1056 (2007).
Kumar, "Ergonomics and biology of spinal rotation", Ergonomics, vol. 47, No. 4, pp, 370-415 (2004).
Kuroyanagi et al., "The lateral wedged insole with subtalar strapping significantly reduces dynamic knee load in the medial compartment" Osteoarthritis and Cartilage, doi:10.10.1016/j.joca.2007.02.004, (2007).
Kusumoto et al., "Intervention study to improve quality of life and health problems of community-living elderly women in Japan by shoe fitting and custom-made insoles", Gerontology, vol. 53, pp. 348-356 (2007).
Lahr et al., "Towards a theory of modern human origons: geography, demography, and diversity in recent human evolution", Yearbook of Physical Anthropology, vol. 41, pp. 137-176 (1998).
Laitman and William, "A review of current concepts on the evolution of the human foot" Foot and Ankle, vol. 2, No. 5, No. 284, pp. 90 (1982).
Larsen et al. "Can custom-made biomechanic shoe orthoses prevent problems in the back and lower extremities? A randomized, controlled intervention trial of 146 military conscripts", J. Manipulative Physiol. Ther., vol. 25, No. 5, pp. 326-331 (2002) Abstract only.
Laitman, "Evolution of the human foot: a multidisciplinary overview" Foot and Ankle, vol. 3, No. 6, pp. 301-304 (1993).
Lakes and Vanderby, "Interrelation of creep and relaxation: a modeling approach for ligaments", Journal of Biomechanical Engineering, vol. 121, pp. 612-615 (1999).
Lakes, "Biomechanics Research: Bone, Ligament, Wood", Biomechanics, 5 pages (2008).
Landorf et al., "Effectiveness of foot orthoses to treat plantar fasciitis: a randomized trial", Arch Intern Med., vol. 166, pp. 1305-1310 (2006).
Landorf and Keenan, "An evaluation of two foot-specific, health-related quality-of-life measuring instruments", Foot Ankle Int., vol. 23, No. 6, pp. 538-546 (2002) Abstract only.
Landorf and Keenan; "Efficacy of foot orthoses. what does the literature tell us?", Journal of the American Podiatric Medical Association, vol. 90, No. 3, pp. 149-158 (2000).
Lantz, "Immobilization degeneration and the fixation hypothesis of chiropractic subluxation", Chiropractic Res Journal, vol. 1, No. 1, pp. 21-46 (1988).
Lauf, "Treating flatfoot" Biomechanics, vol. 3, No. 4, pp. 53-57 (1996).
Lee, "An historical appraisal and discussion of the root model as a clinical system of approach in the present context of theoretical uncertainty", Biomechanics-Clinics in Podiatric Medicine and Surgery, vol. 18, No. 4, pp. 555-599, 603-645, and 647-690 2001.
Lee, "Diagnosis and treatment of adult flatfoot", The Journal of Foot and Ankle Surgery, vol. 44, No. 2, pp. 78-311 (2005).
Leung et al., "Orthotic design and foot impression procedures to control foot alignment", Prosthet. Orthot. Int., vol. 28, No. 3, pp. 254-262 (2004) Abstract only.
Lewis, "The joints of the evolving foot. part I. the ankle joint", Journal of Anatomy, vol. 130, No. 3, pp. 527-543 (1980).
Lewis, "The joints of the evolving foot. part II. The intrinsic joints", Journal of Anatomy, vol. 130, No. 4, pp. 833-857 (1980).
Lewis, "The joints of the evolving foot. part III. the fossil evidence", Journal of Anatomy, vol. 131, No. 2, pp. 275-298 (1980).
Levin, "The tensegrity-truss as a model for spine mechanics: biotensegrity" Online article, www.biotensegrity.com (2007).
Levin, "Biotensegrity, the joint as an inclined plane: the slippery slope", Online article, www.biotensegrity.com (2006).
Levin, "Continuous tension, discontinuous compression: a model for biomechanical support for the body", Bulletin of Structural Integration, vol. 8, No. 1, 6 pages (1982).
Levine et al., "Plantar lateral dislocation of the medial cuneiform: a case report", Foot and Ankle International, vol. 19, No. 2, pp. 118-119 (1998).
Lott et al., "Effect of footwear and orthotic devices on stress reduction and soft tissue strain of the neuropathic foot", Clin. Biomech., vol. 22, No. 3, pp. 352-359 (2007).
Lovett, "A contribution to the study of the mechanics of the spine", American Journal of Anatomy, vol. 2, No. 4, pp. 457-462 (2005).
Lubenow, "Bones of contention: a creationist assessment of the human fossils" pp. 168-173, Baker Books (1992).
Lynch et al., "Conservative treatment of plantar fasciitis: a prospective study", Journal of the Podiatric Medical Association, vol. 88, No. 8, pp. 375-380 (1998).
Maciejewski et al., "Effectiveness of diabetic therapeutic footwear in preventing reulceration", Diabetes Care, vol. 27, pp. 1774-1782 (2004).
Manter, "Movements of the subtalar and transverse tarsal joints" The Anatomical Record, vol. 80, No. 4, pp. 397-410 (1941).
Martin et al., "Mechanical treatment of plantar fasciitis: a prospective study", Journal of the Podiatric Medical Association, vol. 91, No. 2, pp. 55-62 (2001).
Marzano, "Orthotic considerations and footwear modifications following ankle fusions", Techniques in Foot and Ankle Surgery, vol. 1, No. 1, 46-49 (2002).
Mathieson, "Reconstructing root-an argument for objectivity" Biomechanics, vol. 18, No. 4, pp. 683-691 (2001).
McGrath and Finch, "Running the race against injuries: a review of the literature", Monash University Accident Research Centre, Report No. 104, 66 pages (1996).
McCurdy, "Custom orthotics not necessarily better than prefab", Podiatry Today, vol. 18, No. 2, pp. 6-13 (2005).

(56) References Cited

OTHER PUBLICATIONS

McNally, "Ultrasound of the small joints of the hands and feet: current status", Skeletal Radiol., vol. 37, No. 2, pp. 99-113 (2008).
McRitchie et al., "A randomized control trial for evaluating over-the-counter golf orthoses in alleviating pain in amateur golfers", The Foot, vol. 17, pp. 57-64 (2007).
Mein et al., "Physiological regulation through manual therapy" Physical Medicine and Rehabilitation: State of the Art Reviews, vol. 14, No. 1, pp. 1-11 (2000).
Melov et al., "Resistance exercise reverses aging in human skeletal muscle", www.plosone.org (2007).
Mendicino et al., "Roundtable insights on adult-acquired flatfoot", Podiatry Today, vol. 18, No. 6, pp. 34-42 (2005).
Menz et al., "Foot pain in communuty-dwelling older people: an evaluation of the Manchester foot pain and disability index", Rheumatology, vol. 45, No. 7, pp. 863-867 (2006).
Meyer et al., "Metatarsalgia due to insufficient support by the first ray", International Orthopedics, vol. 5, pp. 193-201 (1981).
Michaud and Nawozenski, "The influence of two different types of foot orthoses on first metatarsophalangeal joint kinematics during gait in a single subject", J. Manipulative Physiol. Ther., vol. 29, No. 1, pp. 60-65 (2006) Abstract only.
Mickle et al., "The feet of overweight and obese young children: are they flat or fat?", Obesity, vol. 14, pp. 1949-1953 (2006).
Mickle et al., "Does excess mass affect plantar pressure in young children?", Int. J. Pediatr. Obes., vol. 1, No. 3, pp. 183-188 (2006) Abstract only.
Miles and Ghelashvill, "Polymer-in-a-box mechanism for the thermal stabilization of collagen molecules in fibers", Biophysical Journal, vol. 76, No. 6, pp. 3243-3252 (1999).
Milgrom et al., "A controlled randomized study of the effect of training with orthoses on the incidence of weight bearing induced back pain among infantry recruits",. Spine, vol. 30, No. 3, pp. 272-275 (2005) Abstract only.
Miller "Triplanar intrinsic posting of the cuboid triangle and digital imaging: a new approach to managing lower kinetic chain dysfunction", Online article, http://www.insolepro.co.uk/images/triplanar_intrinsic.pdf., 16 pages (1980).
Moraros and Hodge, "Orthotic survey-preliminary results" Journal of the American Podiatric Medical Association, vol. 83, No. 3, pp. 139-148 (1993).
Morris, "Biomechanics of the foot and ankle" Clinical Orthopedics and related research, vol. 122, pp. 10-17 (1977).
Mueller et al., "Efficacy and mechanism of orthotic devices to unload metatarsal heads in people with diabetes and a history of plantar ulcers", Physical Therapy, vol. 86, No. 6, pp. 833-842 (2006).
Munteanu and Bassed, "Effect of foot posture and inverted foot orthoses on haliux dorsiflexion", JAMA, vol. 96, No. 1, pp. 32-37 (2006).
Murdock, "Proconsul Africanus: an examination of its anatomy and evidence for its extinction in a post-flood catastrophe", TJ, vol. 17, No. 2, pp. 13-15 (2003).
Murphy, "White Paper on TAM and COM'nalysis-add on modules for the F-scan system-biomechanical parameters for analysis and interpretation of foot function and gait", pp. 1-28 (2004).
Myerson, "Adult acquired flatfoot deformity: treatment of posterior tibial tendon insufficiency", The Institute for Foot and Ankle Reconstruction at Mercy. Mercy Hospital, Baltimore, Md., 11 pages (1995).
Nagel, A. et al., "Long Distance Running Increases Plantar Pressure Beneath the Metatarsal Heads A Barefoot Walking Investigation of 200 Marathon Runners" Gait and Posture, www.sciencedirect.com 1-4, (2007).
Napier, "The antiquity of human walking" Scientific American, vol. 216, No. 4, pp. 56-66 (1967).
Nawoczenski and Ludewig, "The effect of forefoot and arch posting orthotic designs on first metatarsophalangeal joint kinematics during gait", J. Orthop. Sports Phys. Ther., vol. 34, No. 6, pp. 317-327 (2004) Abstract only.
Nester et al,, "Kinematics of the midtarsal joint during standing leg rotation" Journal of the American Podiatric Medical Association, vol. 92, No. 2, pp. 77-81 American Podiatry Association, (2002).
Nester et al., "Scientific approach to the axis of rotation at the midtarsal joint", Journal of American Podiatric Medical Association, vol. 91, No. 2, pp. 68-73 (2001).
Nevill and Whyte, "Are there limits to running world records?" Medical Science Sports Exercise, vol. 37, No. 10, pp. 1785-1788 (2005).
Nishi et al., "Isolated plantar dislocation of the intermediate cuneiform bone", The Journal of Bone and Joint Surgery, vol. 86A, No. 8, pp. 1772-1776 (2004).
Nitz et al., "Comparison of muscle spindle concentrations in large and small human epaxial muscles acting in parallel combinations", The American Surgeon, vol. 52, pp. 273-277 (1986).
Novacheck, "The biomechanics of running" Gait and Posture, vol. 7, pp. 77-95 (1998).
Novick et al., "Reduction of plantar pressure with the rigid relief orthosis", J. Am. Podiatr. Med. Assoc., vol. 83, No. 3, pp. 115-122 (1993) Abstract only.
NY Times, National Briefing: Science and Health, "Diabetes Cases increase 15 Percent in 2 Years", by Bloomberg News, 1 page, Published: Jun. 25, 2008.
O'Brien et al., "Estimates of direct medical costs for microvascular and macrovascular complications resulting from type 2 diabetes mellitus in the united states in 2000", Clin. Thel., vol. 25, pp. 1017-1038 (2003).
O'Leary, Effect of cushioned insoles on impact forces during running, Journal of the Podiatric Medical Association, vol. 98, No. 1, pp. 36-41 (2008).
Olson and Seidel, "Evolutionary basis of some clinical disorders of the human foot" Foot & Ankle, vol. 3, No. 6, pp. 322-341 (1983).
O'Malley et al., "Selective hindfoot arthrodesis for the treatment of adult acquired flatfoot deformity: an in vitro study" Foot and Ankle International, vol. 16, No. 7, pp. 411-417 (1995).
Opitz, "Limb anomalies from evolutionary developmental, and genetic perspectives", American Journal of Medical Genetics, vol. 115, No. 4, pp. 231-244 (2002).
Orendurff et al., "The effect of walking speed on center of mass displacement" Journal of Rehabilitation Research & Development, vol. 41, No. 6A, pp. 829-834 (2004).
Orthopaedic Fast Facts, The website of the American Academy of Orthopaedic Surgeons, 2 pages (2007).
Paavolainen et al., "Explosive-strength training improves 5-km running time by improving running economy and muscle power", Journal Applied Physiology, vol. 86, pp. 1527-1533 (1999).
Pack, "On the beauty of the human foot", Journal of the American Podiatry Association, vol. 56, No. 1, pp. 26-29 (1966).
Panjabi, "A hypothesis of chronic back pain: ligament subfailure injuries lead to muscle control dysfunction", European Spine Journal vol. 15, No. 5, pp. 1-17 (2006).
Pawelka et al., "Comparison of two insole materials using subjective parameters and pedobarography (pedar-system)", Clin Biomech., vol. 12, No. 3, pp. S6-S7 (1997) Abstract only.
Payne et al., "Static stance response to different types of foot orthoses" Journal of the American Podiatric Medical Association, vol. 93, No. 6, pp. 492-498 (2003).
Pellow and Brantingham, "The efficacy of adjusting the ankle in the treatment of subacute and chronic grade I and grade II ankle inversion sprains", Journal of Manipulative and Physiological Therapeutics, vol. 24, No. 1, pp. 17-24 (2001).
Percy and Menz, "Effects of prefabricated foot orthoses and soft insoles on postural stability in professional soccer players", J. Am. Podiatr. Med. Assoc., vol. 91, No. 4, pp. 194-202 (2001).
Pfeffer et al., "Comparison of custom and prefabricated orthoses in the initial treatment of proximal plantar fasciitis", Foot & Ankle International, vol. 20, No. 4, pp. 214-221 (1999).
Phillips and Evans, "One pair must last a lifetime. Case studies of foot care in diabetes", Aust. Fam. Physician., vol. 31, No. 6, pp. 546-549 (2002) Abstract only.
Pinzur and Dart, "Pedorthic management of the diabetic foot", Foot Ankle Clin., vol. 6, No. 2, pp. 205-214 (2001) Abstract only.

(56) References Cited

OTHER PUBLICATIONS

Pope, "Americans spend more to treat spine woes", N.Y. Times, (2008).
Pratt, "A critical review of the literature on foot orthoses", Journal of the Podiatric Medical Association, vol. 90, No. 7, pp. 339-341 (2000).
Preuschoft, "Mechanisms for the acquisition of habitual bipedality: are there biomechanical reasons for the acquisition of upright bipedal posture", Journal of Anatomy, vol. 204, No. 5, pp. 363-384 (2004).
Preuschoft, "Body posture and mode of locomotion in early pleitocene hominids", Journal of Primatology, vol. 14, No. 3, pp. 208-240 (1971).
Provenzano et al., "Nonlinear ligament viscoelasticity", Annals of Biomedical Engineering, vol. 29, pp. 908-914 (2001).
Raynor et al., "Are transitions in human gait determined by mechanical, kinetic or energetic factors?", Human Movement Science, vol. 21, pp. 785-805 (2002).
Rau, "Orthotics in the sports chiropractic", Today's Chiropractic, vol. 34, No. 3, pp. 64-69 (2005).
Reiber et al., "Effect of therapeutic footwear on foot reulceration in patients with diabetes" Journal of American Medical Association, vol. 287, pp. 2552-2558 (2002).
Reiber et al., "Effect of therapeutic footwear on foot reulceration in patients with diabetes", JAMA, vol. 287, No. 19, pp. 2552-2558 (2002).
Riche, "A new approach to adult-acquired flatfoot", Podiatry Today, vol. 17, No. 5, pp. 32-46 (2004).
Richmond et al., "Origin of human bipedalism: the knuckle-walking hypothesis revisted", Yearbook of Physical Anthropology, vol. 44, pp. 70-105 (2001).
Riddiford-Harland, "Does obesity influence foot structure in prepubescent children?" Int. J. Obes. Relat. Metab. Disord., vol. 24, No. 5, pp. 541-544 (2000) Abstract only.
Riddle and Schappert, "Volume of ambulatory care visits and patterns of care for patients diagnosed with plantar fasciitis: a national study of medical doctors", Foot Ankle Int., vol. 25, No. 5, pp. 303-310 (2004) Abstract only.
Ridola et al., "The synovial joints of the human foot" Italian Journal of Anatomy and Embryology, vol. 112, No. 2, pp. 61-80 (2007).
Ritchie, "Adult Flatfoot", Podiatry Network.com, 3 pages (2008).
Rome et al., "Heel pad stiffness in runners with plantar heel pain", Clinical Biomechanics, vol. 16, pp. 901-906 (2001).
Rome and Brown, "Randomized clinical trial into the impact of rigid foot orthoses on balance parameters in excessively pronated feet", Clin Rehabil., vol. 18, pp. 6, pp. 624-630 (2004) Abstract only.
Rompe et al., "Evaluation of low-energy extracorporeal shock-wave application for treatment of chronic plantar fasciitis", Journal of Bone and Joint Surgery, vol. 84, No. 3, pp. 335-341 (2002).
Rondberg, "Orthotics in the sports chiropractic practice" World Chiropractic Alliance, Online article, www.worldchiropracticalliance.org/tcj/2005/sep/j.html, pp. 1-3 (2005).
Ross, "Assessing orthotic quality", Podiatry Today, vol. 15, No. 6, pp. 46-51 (2002).
Roxas, "Plantar Fasciitis: diagnosis and therapeutic considerations", Alternative Medicine Review, vol. 10, No. 2, pp. 83-93 (2005) Abstract only.
Sammarco, "The talonavicular and calcaneocuboid joints: anatomy, biomechnics, and clinical management of the transverse tarsal joint", Foot Ankle Clinical Anatomy, vol. 9, No. 1, pp. 127-145 (2004).
Sandala, "The diabetic athlete part two", Biomechanics, vol. 3, No. 4, pp. 73-75 (1996).
Sandberg et al., "Operative versus non-operative treatment of recent injuries to the ligaments of the knee. A prospective randomized study", The Journal of Bone and Joint Surgery, vol. 69, pp. 1120-1126 (1987).
Sanders, "Orthotic management of charcot-marie-tooth disease", Biomechanics, vol. 3, No. 4, pp. 43-44(1996).
Saunders et al., "Factors affecting running economy in trained distance runners", Sports Medicine, vol. 34, No. 7, pp. 465-485 (2004).
Seaman, "Proprioceptor an obsolete, inaccurate word", Journal of Manipulative and Physiological Therapeutics, vol. 20, No. 4, pp. 279-284 (1997).
Severinsen et al., "Atrophy of foot muscles in diabetic patients can be detected with ultrasonography", Diabetes Care, vol. 30, No. 12, pp. 3053-3057 (2007) Abstract only.
Scherer, "Root biomechanics-does it still hold water?" Online article, http://www.podiatrym.com/podiatrymanagement.cfm, pp. 1-7 (2006).
Schleip, "What do scientists tell us about back pain, notes from the fourth world congress on low back and pelvic pain" The Journal of the Rolf Institute, vol. 30, No. 3 (2002).
Schmitt and Largon, "Heel contact as a function of substrate type and speed in primates", American journal of Physical Anthropology, vol. 96, pp. 39-50 (1995).
Schon, "Nerve entrapment, neuropathy, and nerve dysfunction in athletes" Foot and Ankle Injuries in Sports, vol. 25, No. 1, pp. 47-59 (1994).
Sigmon, "Bipedal behavior and the emergence of erect posture in man" American Journal of Physical Anthrpology, vol. 34, No. 1, pp. 55-60 (1971).
Singh et al, "Preventing foot ulcers in patients with diabetes", JAMA, vol. 293, No. 2, pp. 217-228 (2005).
Skliar, "Critique of Podiatric Biomechanics by William Eric Lee, DPM" Biomechanics, vol. 18, No. 4, pp. 685-689 (2001).
Slater et al., "Reduction of digital plantar pressure by debridement and silicone orthosis", Diabetes Res Clin Pract., vol. 74, No. 3, pp, 263-266 (2006).
Smith et al., "New concepts and measures of stability for orthosis-assisted gait" School of Exercise and Sport Science Faculty of Health Sciences, The University of Sydney, Sydney Australia, Online article, www.ifess.org/ifess02/gait_posture/SmithRM.pdf, pp. 1-4 (2002).
Springett et al., "A Clinical longitudinal evaluation of pre-fabricated, semi-rigid foot orthoses prescribed to improve foot function", The Foot, vol. 17, pp. 184-189 (2007).
Stacoff et al., "Biomechanical effects of foot orthoses during walking", The Foot, vol. 17, pp. 143-153 (2007).
Stevens, "DinoMorph: Parametric Modeling of Skeletal Structures" Concepts of Functional, Engineering and Constructional Morphology, vol. 82, No. 1, pp. 23-34 (1996).
Summers, "Borne to run" Natural History, vol. 114, No. 3, pp. 34-35 (2005).
Susman, "Evolution of the human foot: evidence from plio-pleistocene hominids" Foot and Ankle, vol. 3, No. 6, pp. 365-376 (1983).
Tardieu et al., "New method of three-dimensional analysis of bipedal locomotion for the study of displacements of the body and body-parts centers of mass in man and non-human primates: evolutionary framework", American Journal of Physiology and Anthropology, vol. 90, No. 4, pp. 455-475 (1993).
Tayal et al., "Prospective use of ultrasound imaging to detect bony hand injuries in adults" J. Ultrasound Med., vol. 26, No. 9, pp. 1143-1148 (2007) Abstract only.
Taylor and Murphy, "Cervical spine manipulation alters sensorimotor integration: a somatosensory evoked potential study" Clinical Neurophysiology, vol. 118, pp. 391-402 (2006).
Taylor and Lemming, "Neck and back pain" White Paper Virginia Mason Clinic, Seattle, WA, Chapter 9, pp. 242-264 (2001).
Taylor et al., "Endurance training increases skeletal muscle lkb1 and pgc-1 protein abundance: effects of time and intensity", American Journal of Physiological Endocrinal Metab., vol. 289, No. 5, pp. E960-E968 (2005).
Tek Scan, "F-Scan System Accuracy and Repeatability Study"In House White Paper, 8 pages (1999).
Tek Scan, "The Diabetic Foot", In house White Paper, 10 pages (2004).
Terslev et al., "Doppler ultrasound findings in healthy wrists and finger joints before and after use of two different contrast agents", Annals of the Rheumatic Diseases, vol. 64, pp. 824-827 (2005).
Thacker et al., "The impact of stretching on sports injury risk: a systematic review of the literature", Medicine, Science, Sports Exercise, vol. 36, No. 3, pp. 371-378 (2004).

(56) References Cited

OTHER PUBLICATIONS

Thomas, "The diagnosis and treatment of heel pain", The Journal of Foot and Ankle Surgery, vol. 40, No. 5, pp. 329-340 (2001).
Torkki et al., "Surgery vs. orthosis vs. watchful waiting for hallux valgus: a randomized controlled trial", JAMA, vol. 285, pp. 2474-2480 (2001).
Turvey, "Action and perception at the level of synergies" Human Movement Science, vol. 26, pp. 675-697 (2007).
Uematsu, "Thermographic imaging of cutaneous sensory segment in patients with peripheral nerve injury", Journal of Neurosurgery vol. 62, pp. 716-720 (1985).
U.S. Department of Veterans Affairs, "Study findings raise questions on widespread prescribing of diabetic footwear", 2 pages (May 14, 2002).
Van Tulder and Koes, "Chronic low back pain", American Family Physician, 3 pages (Nov. 1, 2006).
Van Schie et al., "Muscle weakness and foot deformities in diabetes", Diabetes Care, vol. 27, No. 7, pp. 1668-1673 (2004).
Van Wingerden et al., "A functional-anatomical approach to the spine-pelvis mechanism: interaction between the biceps femoris muscle and the sacrotuberous ligament", European Spine Journal, vol. 2, pp. 140-144 (1993).
Vasil'ev and Zhelezinskaia, "Topographic anatomic features of radiocarpal joints and carpal articulations", Vestn. Rentgenol. Radiol., vol. 5, pp. 15-21 (2006) Abstract only.
Vaughan et al., "How are we doing: clinical gait laboratories", Biomechanics, vol. 3, No. 4, pp. 69-80(1996).
Vicenzino et al., "Foot orthoses and physiotherapy in the treatment of patellofemoral pain syndrome: A randomised clinical trial", BMC Musculoskeletal Disorders vol. 9, pp. 27, 12 pages (2000).
Vleeming et al., "The function of the long dorsal sacroiliac ligament: its implication for understanding low back pain [Biomechanic]" Spine, vol. 21, No. 5, pp. 556-562 (1996).
Vleeming et al., "The role of the sacroiliac joints in coupling between spine, pelvis, legs and arms", Movement, Stability and Low Back Pain, New York, Churchill Livingstone, pp. 53-71 (1997).
Waddington and Adams, "Football boot insoles and sensitivity to extent of ankle inversion movement", Br J. Sports Med., vol. 37, No. 2, pp. 170-175 (2003).
Walter et al., "A patient satisfaction survey on prescription custom-molded foot orthoses" Journal of the American Podiatric Medical Association, vol. 94, No. 4, pp. 363-367 (2004).
Wang and Crompton, "Analysis of the human and ape foot during bipedal standing with implications for the evolution of the foot" Journal of Biomechanics, vol. 37, pp. 1831-1836 (2004).
Ward, "12 components of biophysics of the fascial tensegrity-matrix system" www.plasmaresources.com/structureandfunction.org/wordpress/?p=21, 8 pages, (2008).
Ward, "Interpreting the posture and locomotion of australopithecus afarensis: where do we stand?", Yearbook of Physical Anthropology, vol. 45, pp. 185-216 (2002).
Waxman et al., "A prospective follow-up study of low back pain in the community", epidemiology, Spine, vol. 25, No. 16, pp. 2085-2090 (2000) Abstract only.

Wearing et al., "Plantar fasciitis: are pain and fascial thickness associated with arch shape and loading?", Phys Ther., vol. 87, No. 8, pp. 1002-1008 (2007).
Weiss, "Spinal ultrasound: clinical correlation of spinal ultrasound and MRI" American Journal of Podiatric Medicine, vol. 6, pp. 123-126 (1996).
Weldon, "Orthotic applications for carbon fiber", Biomechanics, vol. 3, No. 4, pp. 47-51 (1996).
Wernick, "Rethinking neutral position casting-should we be measuring the foot instead of casting it?" Podiatry Management www.podiatrym.com, pp. 77-83 (2002).
Wheeless, "Pes Planus / Flat Foot, Wheeless" Textbook of Orthopaedics, 3 pages (2008).
Whitford et al., "A Randomized controlled trial of two types of in-shoe orthoses in chiidren with flexible excess pronation of the feet", Foot & Ankle International, vol. 28, No. 6, pp. 715-723 (2007).
Williams and Ziff, "Changes in distance running mechanics due to systematic variations in running style" International Journal of Sport Biomechanics, vol. 7, pp. 76-90 (1991).
Williams et al., "Changes in distance running kinematics with fatigue", International Journal of Sport Biomechanics, vol. 7, pp. 138-162 (1991).
Williams and Yakel, "Clinical uses of in-shoe pressure analysis in podiatric sports medicine", Journal of the American Podiatric Medical Association, vol. 97, No. 1, pp. 49-58 (2007).
Williams and Cavanagh, "Relationship between distance running mechanics, running economy, and performance", Journal of Applied Physiology, vol. 63, No. 3, pp. 1236-1245 (1987).
Williams,"Orthotics Q&A: comparing lessons on biomechanics and the realities of clinical experience", Podiatry Today, vol. 19, No. 4, pp. 32-36 (2006).
Withnall et al., "Do shock absorbing insoles in recruits undertaking high levels of physical activity reduce lower limb injury? A randomized controlled trial.", Journal of the Royal Society of Medicine, vol. 99, pp. 32-37 (2006).
Wu et al., "Foot ulcers in the diabetic patient, prevention and treatment", Vasc. Health Risk Manag., vol. 3, No. 1, pp. 65-76 (2007).
Yates and White, "The incidence and risk factors in the development of medial tibial stress syndrome among naval recruits", The American Journal of Sports Medicine, vol. 32, pp. 772-780 (2004).
Zammit et al., "Relationship between positive clinical outcomes of foot orthotic treatment and changes in rearfoot kinematics",. Journal of the Podiatric Medical Association, vol. 97, No. 3, pp. 207-212 (2007).
Zhang et al., "Assessment of human locomotion by using an insole measurement system and artifical neural networks" Journal of Biomechanics, vol. 38, pp. 2276-2287 (2005).
Zipfel and Beger, "Shod versus unshod: The emergence of forefoot pathology in modern humans?", The Foot, vol. 17, pp. 205-213 (2007).
Zographos et al., "Experimental study of the subtalar joint axis preliminary investigation" Surgical Radiology Anatomy, vol. 22, pp. 271-276 (2000).

* cited by examiner to FIG. 3A

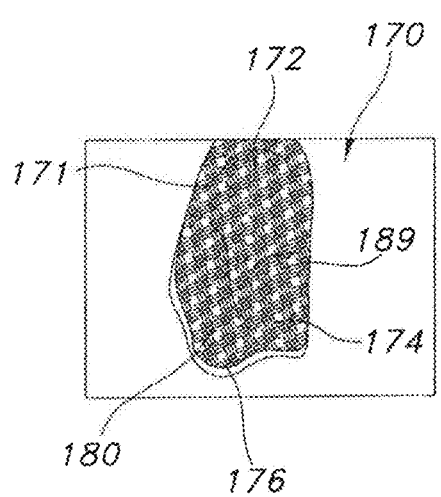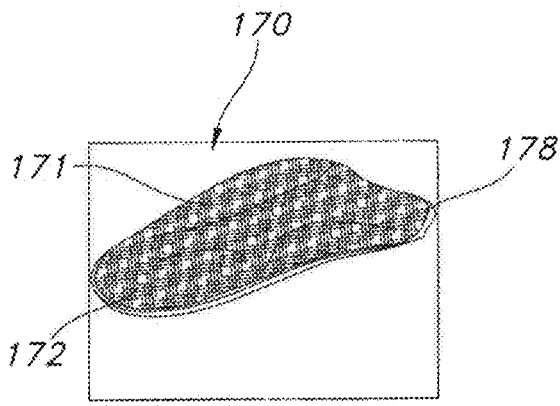
FIG. 14A    FIG. 14B
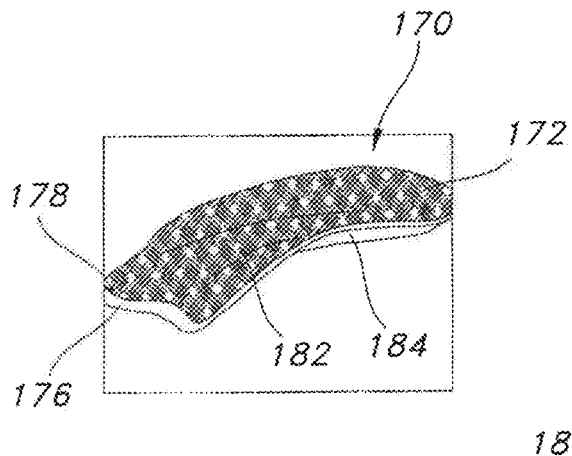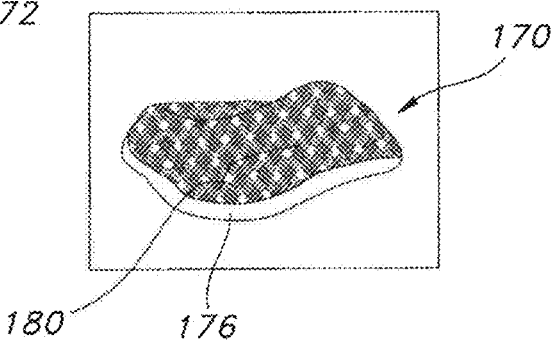
FIG. 14C    FIG. 14D
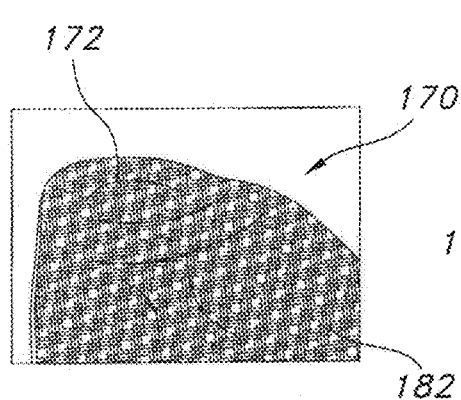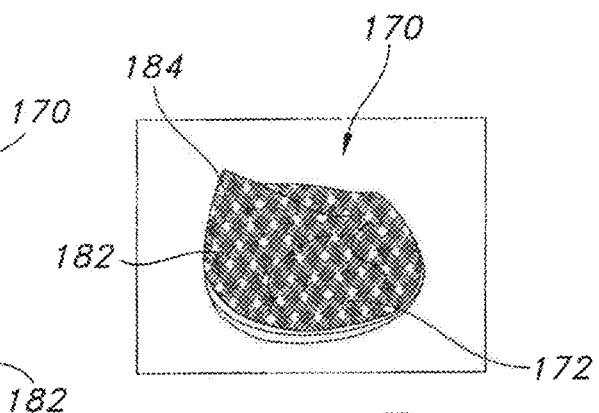
FIG. 14E    FIG. 14F

SYSTEMS FOR DESIGNING A FOOT ORTHOTIC

CROSS-REFERENCE TO RELATED APPLICATIONS

This application is a continuation of U.S. application Ser. No. 12/355,513, filed Jan. 16, 2009, now allowed, which claims priority to U.S. provisional application No. 61/011,640, filed Jan. 17, 2008, and to U.S. provisional application No. 61/038,020, filed Mar. 19, 2008, both of which are incorporated by reference herein in their entirety.

TECHNICAL FIELD

The subject matter described herein relates to systems for the design of a foot orthotic and to a foot orthotic designed using the system. More particularly, the subject matter is directed to systems that obtain and utilize a digital anatomy of one or more structures in a foot of a patient for the design of one or more custom foot orthotics, to be used, in some embodiments, in a restorative treatment plan.

BACKGROUND

Foot orthotics are typically designed based on an image of the plantar surface of a patient's foot. Standard foot orthotics attempt to treat foot or arch pain by providing cushioning, stability or support, sometimes attempting to adjust or stabilize movement about the subtalar joint. Prior to about 1950, there was little to no standardization in the methods used to treat mechanically-induced foot pain. A standardized approach to the design of foot orthoses was introduced in 1954, when Merton L. Root, DPM, revolutionized the field with the theory of the Subtalar Neutral Position (STNP) (Lee, 2001, "An Historical Appraisal and Discussion of Root Model as a Clinical System of Approach in the Present Context of Theoretical Uncertainty," *Clinics in Podiatric Medicine and Surgery*, 18(4)).

The subtalar joint is the joint between the talus and calcaneus bones. Subtalar neutral is where the subtalar joint is neither pronated nor supinated and its importance was based on observations of what Root subjectively deemed to be "normal" feet. According to Root's theory, correction of a foot to a "normal" position involves placing of only the subtalar joint into a 'neutral' position, the so-called subtalar neutral position or STNP. Root's theory involved only correction of the subtalar joint and did not involve manipulation or correction to other bones or joints in the foot. Further corrections, postings and wedges were then added to an orthotic after the subtalar joint was placed in neutral position to compensate for any perceived abnormalities. In the present application, the subtalar joint is not a controlling element; rather it is an adaptive joint governed by the position of the joints distal to it. The subtalar joint functions in synergy with other foot structures to allow the foot to adapt to an infinitely variable topography, within physiologic tolerances.

There are two basic types of custom orthoses made today; accommodative and functional. An accommodative orthosis is typically made from a soft or flexible material that cushions and "accommodates" any deformity of the foot. This cushioning also results in some dissipation of the forces required for efficient gait that ordinarily would be transmitted up the kinetic chain. In addition to force dissipation, accommodative orthosis made of EVA and similar soft materials are unable to control foot mechanics. A functional orthosis is one that controls joint movements and/or foot position. Because they are rigid, clinicians utilize these orthoses to hold the foot in a position they deem therapeutic. This is problematic because the foot must be allowed to continually adapt to the ground in order to operate efficiently. For the manufacture of both types of orthoses, the plantar surface of the patient's foot is captured and its mirror image is produced on the surface of the orthotic device that contacts the patient's foot. Materials used to make orthotic devices designed in accord with Root's theory are typically both strong and rigid, to support the patient's weight in adorable manner, as the foot cannot bear the weight itself. Such orthotics abnormally maintain the foot's arch throughout gait, with the orthosis supporting the body's weight and compressing the soft tissue between the bones and the orthosis. An ideal configuration for an orthotic device that is beyond the capability of current functional or accommodative orthoses, would adjust the bones of the foot to create an internal load-bearing structure that is self supporting, bears weight on the calcaneus and metatarsal heads, and enables the foot to adapt to uneven topography.

In practice today, most functional orthotic devices are designed to establish STNP and maintain it from heel strike to the beginning of toe-off. Capturing and maintaining STNP is too simplistic an objective to apply to the complicated kinematics of the foot with its 33 joints, 28 bones, supporting ligaments, tendons, and other structures. Under Root's SNTP theory, and other models of foot function such as Rotational Equilibrium Theory, Sagittal Plane Theory, and the Tissue Stress Model, little, if any, consideration is given to correcting the underlying pathologic changes to foot structure and function. While functional and accommodative orthotics may temporarily decrease foot pain due to restricting pathologic range of motion and in cushioning the foot, they necessarily cause pathologic gait, and this approach will inevitably cause pain in other joints in the foot, leg, pelvis and/or back as they compensate for this abnormal motion. There remains a need for improved methods and systems for designing foot orthotics, and for improved foot orthotics to correct and/or restore the ideal alignment and/or positioning of foot structures.

SUMMARY

In a first aspect, a system for obtaining a restored bone profile of a foot is provided. The system comprises a surface for receiving a plantar surface of the foot; and a pin matrix comprising a plurality of individual pins which can be independently raised from the surface to engage the plantar surfaces and compress tissue against bones of the foot.

In one embodiment, the system comprises a plurality of drivers for the pins, wherein the drivers are coupled to the individual pins to raise each individual pin at a known or controlled pressure. In some embodiments, the drivers each comprise a piston driven by a pressure source. In certain embodiments, a common pressure source is connected to each of the pistons. In other embodiments, a plurality of pressure sources with at least one pressure source are connected to each piston.

The drivers, in one embodiment, comprise a servo-controlled motor adapted to raise an associated pin by preselected distances. In other embodiments, the drivers comprise a constant force spring.

In other embodiments, the pin matrix includes from one to four rows of pins which are configured to span a lateral band of the plantar surface. In one embodiment, the lateral band has a width in the range from 0.5 cm to 2 cm.

In one embodiment, the system further comprises a carriage which holds the pin rows, wherein the carriage is mounted to be translated across the surface to sequentially engage the pins against successive lateral bands.

In another embodiment, the system further comprises a plurality of sensors for determining a penetration depth of each pin as said pin is raised upward from the surface. In still another embodiment, the system further comprises a controller connected to the drivers, carriage, and sensors. In various embodiments, the controller is programmed to sequentially position the carriage, raise the pins against the tissue at one or more pressures at each sequential carriage position, and collect the depth of pin penetration into the tissue at each pressure and each position. In another embodiment, the system further comprises sensors for determining a penetration pressure of each pin as said pin is raised upward from the surface, wherein the pressure sensors are connected to the controller.

In another aspect, systems for design of an orthotic device are provided. Such systems can comprise a platform comprising a plurality of independently moveable gauging elements in contact with a foot placed on the platform; a display capable of displaying a digital anatomy of the foot; and a computer program for analysis of the digital anatomy and evaluation of the relationship between two or more bones in the foot, and for determining an adjustment to one or more gauging elements in the platform (or bed).

In one embodiment, the computer program can obtain the digital anatomy upon application of pressure to one or more gauging elements in the bed when in contact with the foot.

In another embodiment, the system can comprise one or more subsequent analyses of a digital anatomy to re-evaluate the relationship between two or more bones in the foot over time. The computer program can determine an adjustment of one or more gauging elements in the bed for repositioning of one or more bones in the foot, and can send a signal to one or more of the moveable gauging elements to move the one or more gauging elements to an adjusted position. The bed having adjusted gauging element(s) can be used to design and/or fabricate an orthotic device for repositioning of at least one bones in the foot. In one embodiment, a tarsal bone or a metatarsal bone is repositioned.

In other embodiments, the system can comprise a means for transmitting the digital anatomy to a remote location. In other embodiments, the computer program can comprise executable instructions that obtain a digital anatomy of a foot; analyze the digital anatomy to evaluate the relationship between two or more bones in the foot; determine an adjustment to one or more tarsal bones; and send a signal to one or more moveable gauging elements on the bed to effect movement of one or more gauging elements to fabricate an orthotic device for achieving the repositioning of one or more bones.

In yet another embodiment, the system for design of an orthotic device can comprise a bed for contacting a foot; a display capable of displaying digital anatomy of the foot; and a computer program, for analysis of the digital anatomy and evaluation of the relationship between two or more bones in the foot, and for determining an adjustment to one or more bones in the foot.

Also provided is a method performed in a computing system, comprising obtaining pressure and/or elevation data from gauging elements in contact with a patient's foot when placed upon a foot bed; converting the pressure and elevation data to a graphic image of a digital anatomy for display and recording on a computer readable medium; analyzing the digital anatomy for congruency of one or more joints in the patient's foot; comparing an initial bone state to a desired restored bone state; computing a movement path between the initial bone state and the desired restored bone state according to minimum movements criteria; and determining adjustments of the gauging elements needed to move one or more bones along the movement path. In some embodiments, the method further comprises persistently storing the determined adjustments. In some embodiments, the method further comprises moving the gauging elements in accordance with the determined adjustments.

In one embodiment, the foot bed is on a movable carriage, and a plurality of gauging elements on the carriage contact a foot held in a static position, the plurality of gauging elements moving progressively from heel to toe or vice versa, to obtain a digital image of the foot.

Also described in another aspect is a method for design of an orthotic device, in which a digital anatomy of a patient's foot is obtained and analyzed using the system described herein, and a relationship between two or more bones in the foot evaluated, resulting in the identification of one or more tarsal bones for repositioning by the orthotic device.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

FIGS. 14A-14F show various views of a foot orthotic, designed in accord with the methods described herein, to restore the position of one or more foot structures in the midfoot region of a right foot.

DETAILED DESCRIPTION

I. Definitions

Figure 1:
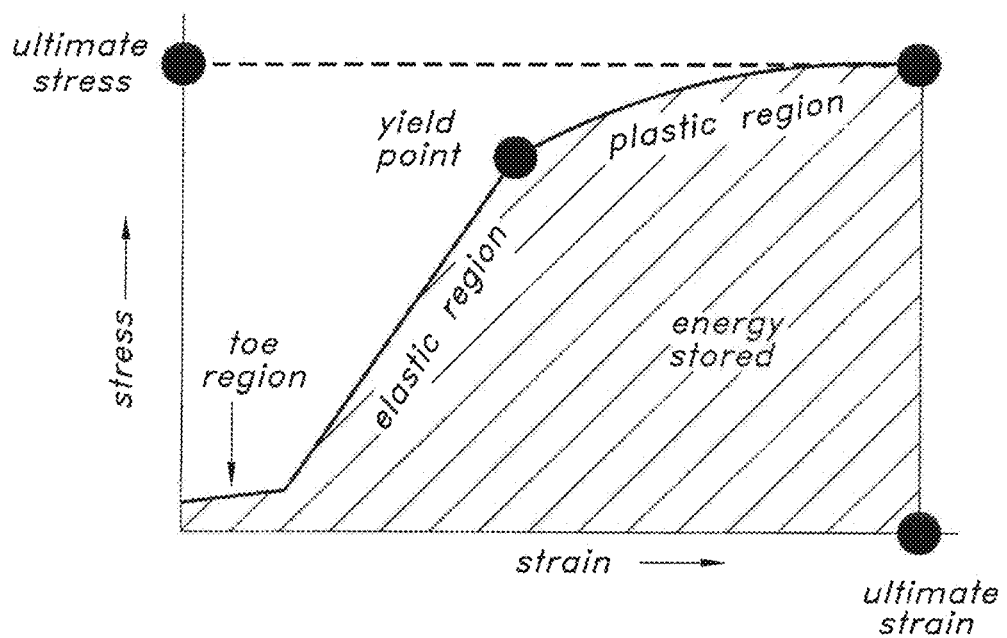
FIG. 1 is an illustration taken from the prior art showing a stress-strain curve of collagen fiber.

As used throughout the present disclosure, the technical and scientific terms used in the descriptions herein will have the meanings commonly understood by one of ordinary skill in the art, unless specifically defined otherwise. Accordingly, the following terms are intended to have the following meanings:

As used in this specification and the appended claims, the singular forms "a," "an," and "the" include plural referents unless the context clearly indicates otherwise. Thus, for example, reference to a patient's "foot" can include both feet, reference to an "orthotic device" includes a single device as well as two or more of the same or different devices, and reference to a "tarsal bone" refers to a single tarsal bone as well as two or more tarsal bones. The use of "or" should be understood to mean "and/or" unless stated otherwise. Similarly, "comprise," "comprises," "comprising" "include," "includes," "including," "has," "have" and "having" are interchangeable and not intended to be limiting. It is also to be understood that where descriptions of various embodiments use the term "comprising," those skilled in the art would understand that in some specific instances, an embodiment can be alternatively described using language "consisting essentially of" or "consisting of."

As used herein, "orthosis" or "orthotic device" refers to a device or appliance to be worn by a subject, in particular a human subject, typically to achieve restoration of optimal joint congruency and physiologic function to a subject's foot. In some instances, the orthotic device can be worn inside footwear. In some instances, the orthotic device can be worn as footwear or other orthopedic device.

"Congruency" of the joint surfaces of the foot bones refers to the reciprocity of the joint articular surface shapes, sometimes assessed by observing and/or measuring the joint space volume. An incongruent joint can be caused, for example, by interposed soft tissue, plastic deformation of ligaments or gross instability from torn ligaments or fracture. The phrase "relationship between bones in the foot" refers to the relative positions of bones within a foot and/or their congruency.

The human "kinetic chain" consists of the musculoskeletal and neuromuscular systems that interact to produce maximally efficient motion under given conditions. The difference between an open and closed kinetic chain is that in an open chain, the body can produce force greater than the inertia of the resistance. In a closed kinetic chain the body cannot produce force greater than the inertia of the resistance, e.g. a leg, loose in space vs. fixed against a hard, immovable surface such as the ground.

As used herein, "digital anatomy" refers to digitized information about the measurement of the static anatomical positions of and relationships between bones, muscles, tendons, ligaments, fascia, nerves, skin and/or other structures within a foot, and can further encompass associated kinetic information about a digital physiology and/or digital pathophysiology, which can be obtained from a foot in a dynamic state, or predicted by a computer system starting from a static measurement of the digital anatomy. A digital anatomy is obtained, for example, using a footbed pin sensor array in communication with a computer and appropriate software, or imaging techniques, including but not limited to magnetic resonance imaging, laser scanning, ultrasound, x-ray, etc. The digital anatomy described herein can be stored in computer-readable form, in a preferred embodiment. The digital anatomy is generally capable of being represented visually and/or graphically on a computer screen or video monitor. The digital anatomy can then be analyzed by the computer to determine the foot's physiology, that is, its ability to efficiently perform weight bearing and locomotion. This physiology can be illustrated by animating the body parts in 3D space, or recording a series of static images in a flipbook video in any one of several popular formats, (for example, but not limited to mpg, avi or quicktime video). This illustration can be customized for individual patients, and the digital physiology can be stored and transferred remotely for viewing, education, treatment and/or manufacturing purposes. Once a foot's current condition is determined, i.e., once the static measurement of the anatomical positions of and relationships between one or more foot structures is determined, an evaluation of the risks for new pathophysiology of the foot and also up through the kinetic chain to the back and neck is performed by the computer. The computer will identify foot pathophysiologies that may lead to pathologic conditions including, but not limited to, heel spurs, acquired flat foot, hip pain and idiopathic back pain. This pathophysiology is illustrated by animating the body parts in 3D space, or recording a flipbook video in a popular format, and such digital pathophysiology can be stored and transferred remotely for viewing, education, treatment and/or manufacturing purposes.

"Tarsal bones" refers to the seven foot bones including the calcaneus, talus, cuboid, navicular, medial cuneiform, middle (intermediate) cuneiform and lateral cuneiform bones. "Plantar" refers to the sole of the foot, and the phrase "plantar aspect of the calcaneus" refers to the plantar- or sole-facing surface of the calcaneus bone, commonly known as the heel bone.

"Forefoot" refers to the five metatarsal bones and the phalanges (the toes). As a point of reference, the first metatarsal bone typically hears the most weight in the forefoot and plays a role in propulsion.

"Midfoot" refers to five of the seven tarsal bones (the navicular, cuboid, and the three cuneiforms). The distal row of the midfoot contains the three cuneiforms and the cuboid. The proximal row of the midfoot consists of the cuboid and the navicular. The three cuneiforms articulate proximally with the navicular bone.

"Rearfoot" refers to the talus and the calcaneus. The calcaneus is the largest tarsal bone, and forms the heel. The talus rests on top of the calcaneus and forms the subtalar joint, which is the joint below or distal to the ankle joint.

There are four arches of the foot. The "medial longitudinal arch" includes the calcaneus, talus, navicular, the lateral, middle and medial cuneiforms, and the first three metatarsals. In an ideal foot, the medial longitudinal arch is the highest of the three arches. The "lateral longitudinal arch" includes the calcaneus, cuboid, and the fourth and fifth metatarsals. The lateral longitudinal arch is typically lower and flatter than the medial arch. The two transverse arches are the "transverse tarsal arch" (comprising the cuneiforms, the cuboid and the five metatarsal heads) and the "transverse metatarsal arch (comprising the 5 metatarsal heads). Some sources say that there is only one transverse arch which involves only the tarsals.

"First Ray" refers to the navicular, medial cuneiform, first metatarsal and the great toe.

"Lateral Column" refers to the calcaneus bone, cuboid bone and fourth and fifth metatarsals.

"Medial Column" refers to the talus, navicular, middle and medial cuneiforms and first and second metatarsals. Some texts also include the lateral cuneiform and third metatarsal.

"Stress" refers to the force that causes deformation and can act as tension, compression or sheer.

"Strain" refers to a measure of the degree of deformation caused by stress.

"Elastic Modulus" refers to the ratio of stress to strain and refers to the nature of the deformation or stiffness of the material.

"Plastic deformation" refers to the ability of ligaments, tendons and fascia, as tensile structures with specific viscoelastic properties, to be damaged or to deviate from an ideal, unstressed position. It is a permanent, non-recoverable deformation. These viscoelastic properties, along with the size of the structure, dictate the magnitude of the forces required to produce injury that ranges from microfractures to catastrophic failure. To permanently damage or tear a ligament or other collagenous fiber typically requires a force at or above the threshold at which the structure in question can resist for approximately one-third of a second in duration. For example, a cruciate ligament may tear when a football player is hit hard on the side of the knee due to the brief, but high force of the insult. Alternately, a submaximal stress for more than 20 minutes has been shown to produce permanent stretch of the affected ligaments, known as plastic deformation. In addition, microfailure can occur within the range of motion if frequent loading is imposed on an already damaged structure. As another example, a person who works, walks, dances or shops for long periods of time, until his or her feet hurt, can sustain physical and potentially permanent damage to ligaments and tendons that can lead to an abnormal gait. As illustrated in the stress-strain curve shown in FIG. 1 (Cavanagh, A., *Neuromechanics of Human Movement*, R. Enoka publishers, p. 82, 189, 192-193, 1994), the "toe region" of the graph represents a normal stretch and return elasticity of ligaments and tendons. Here the "curl" in the conformation of the collagen protein molecule is maintained. In the "elastic region" of the graph, this curl has been stretched out, but permanent damage does not occur. In other words, a tendon/ligament undergoing stress and strain forces within the elastic region of the graph should fully recover when the load is removed (unless it was already damages in which case repeated loading in this range can result in further damage). Hysteresis (energy lost as heat during the recoil from the stretch) occurs anywhere to the left of the solid line up to the dotted line which denotes catastrophic failure. Above the "yield point," irreversible strain occurs.

"Creep" refers to plastic deformation and/or permanent strain in a tissue that can occur over time as a result of application and maintenance of a stress at a set level.

"Pin bed" refers to a bed or box structure having an array of gauging elements, such as vertically displaceable sensing pins, on which a patient's foot can be placed.

As used herein, "computer-controlled moveable object" can refer to a pin bed, a foot plate, or other surface upon which a plantar surface of a patient's foot is placed for obtaining a digital anatomy. Alternatively, and as will be clear from the context, a computer-controlled moveable object can also refer to the individual gauging elements, such as a pin in a pin bed.

Figure 2:
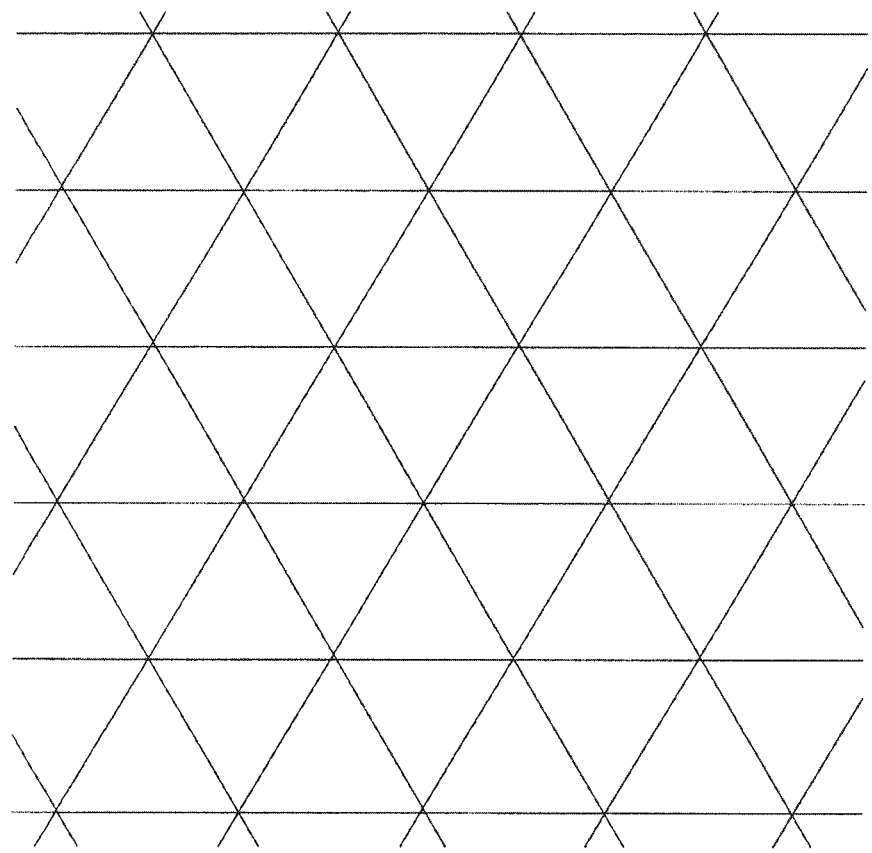
FIG. 2 provides an illustration of an offset triangular grid.

In the context of the present teachings, "offset triangular grid" refers to an isometric grid formed by arranging gauging elements on the two-dimensional planar surface, such as a pin bed, in a regular equilateral triangle pattern. The gauging elements are found at the angle of each equilateral triangle in the grid, as illustrated in FIG. 2.

"Display" refers to a computer screen, video monitor, or other device capable of presenting an image to a viewer. "Display is capable of being manipulated" means that the image can be adjusted, elements added or moved on the screen or monitor to simulate, predict the effects of, or prescribe various adjustments to image, which in one embodiment can be a bone or soft tissue of a foot.

"Electronically transmitting the digital anatomy" refers to the act of conveying the digitized anatomical information to a receiver or storage device, which may reside at a site remote from that at which the digital anatomy originates. Similarly, digitized anatomical information may be sent from a receiver or storage device to a site at which a digital anatomy can be obtained, and/or to a site at which an orthotic can be manufactured.

"Data compression" refers to the process of encoding information using fewer bits (or other information-bearing units) than an unencoded representation would use through use of specific encoding schemes.

"Securing" or "security encoding" refers to the process of encrypting information for protection of the digital anatomical information.

"Initial bone state" refers to the relationships of the bones in a patient's foot in a first, unrestored configuration/relationship before adjustment or manipulation of the bones, such as by treatment with an orthotic designed in accord with the present methods and systems. "Restored bone state" refers to the configuration/relationship of the foot bones that is different from an initial bone state, and in a preferred embodiment refers to the configuration/relationship of foot bones that is a physiologically or medically desired position. "Intermediate bone state" or "intermediate state" refers to configuration/relationship of a patient's foot bones that is between the initial bone state and a restored bone state.

An image of a foot can be obtained using a means of imaging selected from, for example but not limited to, magnetic resonance imaging (MRI), computed tomography (CT), radiologic imaging such as x-rays, ultrasound imaging, infrared imaging, or any variations or combinations thereof.

"Superimposition of the digital anatomies" refers to placement of an image or video representing a second digital anatomy on or over a first image or video representing a digital anatomy, for comparison of two or more digital anatomies. In some embodiments, the superimposition of the digital anatomy images aligns one or more bones in each image. As can be appreciated, superimposition of two images permits assessment of differences between an initial and an intermediate or a restored bone state, and informs the measurements and/or calculations for design of an orthotic to reposition a foot bone.

"Simulation of a movement path" or "defining one or more movements of any bone to move from an initial bone state to the desired restored bone state" refers to the process of measuring or calculating the extent of movement of one or more bones needed to reposition the one or more bones from an initial or intermediate bone state at a given time point to an intermediate or restored bone state at a later time. The movements can be a distance in one or more of the X, Y, Z directions, or can be angular movements around the X, Y, Z axes.

"Six degrees of freedom" or "6DoF" refers to movement in three dimensional space, i.e., the ability to move forward/backward, up/down, left/right (translation in three perpendicular axes) combined with rotation about three perpendicular axes (yaw, pitch, roll). As the movement along each of the three axes is independent of each other and independent of the rotation about any of these axes, the motion has six degrees of freedom. In the context of the present disclosure, 6DoF typically refers to the movement of one or more bones of the patient's foot during repositioning.

"Timer for scheduling a subsequent obtaining of a digital anatomy or follow-up appointment" refers to a component of the system in which a desired length of time for treatment with an orthotic is assessed and the next step in treatment, such as an appointment with the treating clinician or physician to monitor progress or to design a new orthotic, is prescribed.

"Treatment plan" refers to the design of one or more foot orthosis, each of which is to be worn by a patient to achieve a desired repositioning of a foot bone.

"Labeled in order of use" refers to markings on two or more foot orthoses indicate the sequential order in which the two or more orthoses are to be worn.

"Progressively wearing" refers to the sequential wearing of two or more foot orthoses by the patient.

Figure 13A:
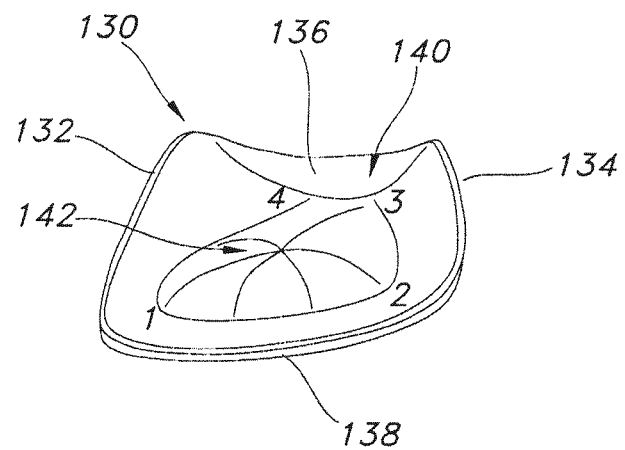
FIG. 13A illustrates an exemplary orthotic device.
Figure 13B:
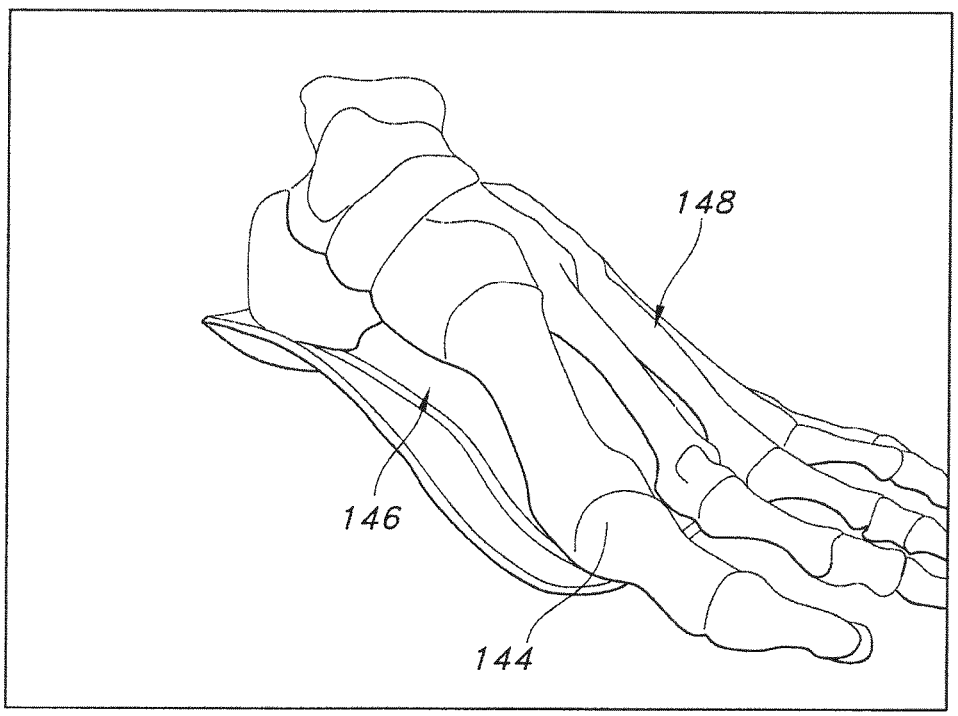
FIG. 13B shows a skeleton of a foot placed on an exemplary orthosis.
Figure 13C:
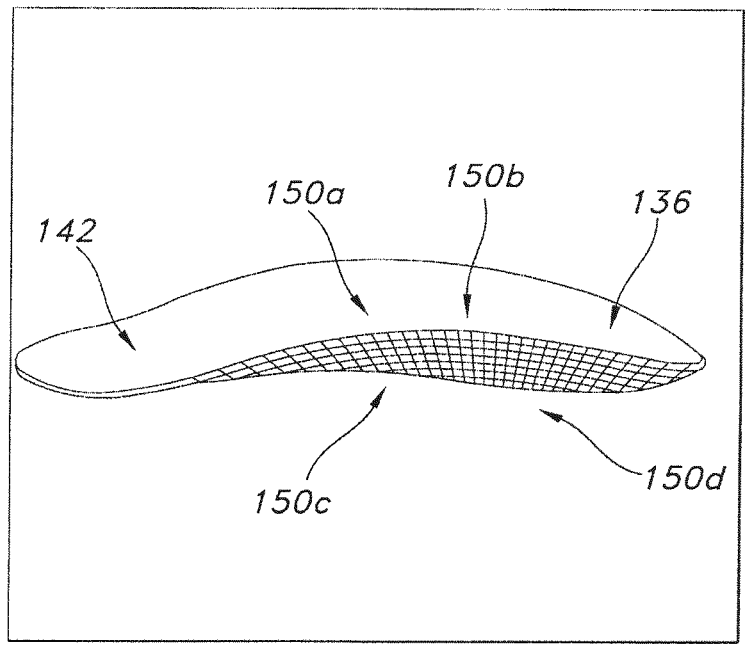
FIG. 13C shows a side view of an exemplary orthosis with a high lateral trim line.

"Saddle" refers to the shape of the orthosis that corresponds to the foot structures supporting the transverse tarsal arch. In one embodiment, an ideal saddle is convex in the sagittal plane and concave in the frontal plane, and is slightly higher on the medial side. "Cuboid triangle post" refers to the foot structures under the metatarsals. FIGS. 13A-13C discussed below illustrate these terms.

"Ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychological evaluation.

When a range of values is provided, it is understood that each intervening value, to the tenth of the unit of the lower limit unless the context clearly dictates otherwise, between the upper and lower limits of that range is also specifically disclosed. Each smaller range between any stated or intervening value in a stated range and any other stated or intervening value in that stated range is encompassed by the disclosure. The upper and lower limits of the smaller ranges can be independently included or excluded in the range, and each range where either, neither or both limits are included in the smaller ranges is also encompassed by the disclosure, subject to any specifically excluded limit in the stated range. Where the stated range includes one or both of the limits, ranges excluding either or both of those included limits are also included.

II. Systems for Design of a Foot Orthotic

The section headings used herein are for organizational purposes only and are not to be construed as limiting the subject matter described in any way.

The present teachings are directed to systems, and methods of using the systems, for diagnosis and evaluation of plastic deformation occurring in the tensile structures of a patient's foot, and for treatment of such plastic deformation, using a custom foot orthotic device designed in accord with the systems and methods.

A. Foot Anatomy

The method described herein for design of an orthotic device and restoration of a foot structure takes into consideration foot structures in addition to the subtalar joint. The foot has 28 bones, including the two sesamoid bones under the great toe, 33 joints and a large number of articular surfaces within the joints, in addition to soft tissues such as muscles, tendons and ligaments. The methods described herein take into consideration that plastic deformity of the ligaments and tendons allows bones in the midfoot to slip downward. When this happens, the articular surfaces of the involved bones are no longer congruent. In many cases this leads to a rigid midfoot that cannot flex when necessary and to hypermobile joints in the forefoot and the rearfoot to compensate for the rigid midfoot. A patient's foot whose midfoot joints are incongruent will further pronate (flatten) under the patient's weight, as without the proper anatomical configuration, the foot muscles continue to weaken and the tendons/ligaments continue to creep.

This concept is illustrated in FIG. 1. Physiologic changes occur when viscoelastic structures, such as ligaments and tendons of a foot, undergo stress and strain. A viscoelastic structure placed under any stress that is below the threshold of catastrophic failure yet above a level of stress where it can return to normal position with no damage, will obtain some degree of plastic deformation. If the same stresses continue, plastic deformation will continue as well. As the joint spaces of the foot are narrow it takes little plastic deformation of the supporting ligaments to negatively alter the joint(s) congruency as once the ligaments creep, the bones are no longer held securely in place and will displace according to the forces placed on them such as by the force of gravity. This eventually results in fixation of the joint(s) as their surfaces wedge against one another. This wedging effect particularly occurs with the midfoot tarsal bones and inhibits physiologic foot function causing a cascade of abnormal motion that result in further plastic deformation, more fixations and damage to the articular cartilage of the involved joint(s).

As will become apparent from the description of the method herein, an orthotic device designed in accord with the method restores, rather than merely supports, the midfoot and any midfoot deformities. Several embodiments of the present disclosure are described in detail hereinafter. These embodiments can take many different forms and should not be construed as limited to those embodiments explicitly set forth herein. Rather, these embodiments are provided so that this disclosure will be thorough and complete, and will fully convey the scope of the present disclosure to those skilled in the art.

The presently disclosed methods and systems for design of a foot orthotic and restoration of one or more foot bones is based, at least in part, on an understanding of foot anatomy, and, in particular on: (1) an intricate pattern of Internal Tarsal Ligaments (ITL linkages). This chain of ligaments includes ligaments between (i) the cuboid and the lateral cuneiform; (ii) the lateral cuneiform and the middle cuneiform; and (iii) the middle cuneiform and the medial cuneiform, as well as (2) the lateral cuneiform, navicular and cuboid (LCNC) complex. The ITL linkages play a role in efficient ambulation and the bones of the LCNC complex function in a specific way during stance phase of ambulation. These findings and their role in restoration of foot function will be detailed below.

Plastic deformation of the supportive structures in the foot is caused through normal wear and tear and through accelerated stresses, such as modern footwear, hard flat surfaces, distance running, obesity, aging, etc. These conditions cause the midfoot to begin to collapse due to the plastic deformation of its ligaments, tendons and fascia. Two of these supportive structures are the long and short plantar ligaments. Strain of these two ligaments allows the calcaneus to plantar flex, at the same time the medial arch decreases in height causing the head of the first ray to increase its distance from the calcaneus.

This results in forefoot abduction and subsequent eversion of the calcaneus, also known as a pronated foot. As the calcaneus plantar flexes, the calcaneocuboid joint widens on the plantar aspect. This allows the cuboid to over-rotate when the lateral column bears weight. Over-rotation of the cuboid deforms ITL linkages by preventing the lateral cuneiform from being pulled into a notch between the cuboid and the navicular. A consequence of these actions is that the medial and lateral columns cannot lock together to form a rigid lever for toe off. As weight moves medially during gait, ground force reaction on the medial column is not met with resistance that results in inefficient energy transfer and pathologic gait. Changes to the midfoot at this point can be visible to the naked eye, and dubbed, in lay terms, a "flat foot". Over time, this plastic deformation of the tensile structures in the foot allows the medial column tarsal bones to drop far enough that they become wedged against one another. As the medial column tarsal bones become wedged, the tensile structures in the rearfoot and forefoot must compensate and therefore undergo plastic deformation. In this case, instead of the bones becoming jammed against one another, they become hypermobile. The paradoxical result is a rigid midfoot with overall foot hypermobility. In some cases, the lateral column collapses due to strain of the tensile structures, further keeping the medial and lateral columns from locking together via the lateral cuneiform (as in the ideal LCNC complex). If the cuneiforms fixate but do not collapse, functional halux limitus is observed, or bunion formation without excessive pronation. When the medial column begins to collapse causing the distance between the calcaneus and the first metatarsal head to further increase, plantar fasciitis can occurs. In extreme cases, a Charcot deformity secondary to, for example, trauma to the foot is observed. In these cases, the entire tarsal complex collapses, i.e., the transverse tarsal arch has a decreased height, with patients presenting with flat, forefoot abducted feet having calcaneal eversion.

While these cases represent a spectrum of presentations possible with midfoot tensile structure plastic deformation, and they may appear to be vastly different in nature, they have similar causality in the sequence of events. The calcaneus loses plantar angle, which allows the cuboid to over rotate when the lateral column bears weight. When this happens, neither the ITL nor LCNC complex can activate correctly, thus the medial and lateral columns cannot act together when needed. Mostly or fully restoring proper anatomical configuration of the midfoot tarsal bones and dynamically (i.e. while moving through a range of motion) supporting them in the proper configuration will ameliorate pathologies in gait, and largely or fully re-establish a physiologic gait that is closer to optimal for that individual. From the perspective that the human body is a tensegrity structure—that is, a self-stabilizing structure where tension is continuous and compression is discontinuous—an objective in one embodiment is to realign the compressive units (the bones) so that the tensile units (ligaments, tendons, muscles) may contract or extend to produce a desired tension in order to maintain the tensegrity structure and maximize the force transfer through the kinetic chain.

B. Methods and Systems for Design of an Orthosis

Provided herein, in one embodiment, is a method to evaluate a patient's foot and to design an orthotic device that restores optimal desired anatomical configuration of midfoot tarsal bones, and dynamically supports the midfoot tarsal bones in a configuration that re-establishes a desired physiologic gait, e.g., a gait that alleviates a symptom suggestive of deformation in a foot anatomical configuration. A system for design of the orthotic device in accord with the method is also provided. The method and the system are now to be described with reference to FIGS. 3-11.

In the method, a patient experiencing foot pain or another symptom suggestive of a deformation in a foot anatomical configuration is provided. A digital anatomy or orthotic profile of the patient's foot (or feet) is obtained, and the digital anatomy is analyzed to evaluate a relationship between two or more bones in the foot. Based on the analysis, one or more tarsal bones are identified for repositioning to restore a desired anatomical configuration to the foot by one or more orthotic devices.

In one embodiment, the system for application of the method is comprised of a in matrix comprising a plurality of moveable pins, the pins moveable for contact with a plantar surface of a foot placed above or on the matrix. In some embodiments, a display in the system is capable of displaying a digital anatomy of the foot, based on positional information of the pins' interaction with the foot. In a preferred embodiment, a computer program in the system analyzes the digital anatomy and evaluates a relationship between two or more bones in the foot, and determines an adjustment to one or more pins in the pin bed to achieve a corresponding adjustment to one or more foot bones. In some embodiments, the adjustments are made to midfoot tarsal bones.

The system has robust measurement, analytical, diagnostic and adjustment capabilities for designing and optionally making custom orthotics. The system measures, analyzes and diagnoses, and adjusts the bones and tensile tissues (ligaments, tendons and fascia) in a patient's foot. The system has the capabilities for mapping a foot surface topography and/or measuring pressure points on the foot plantar surface, and additionally has the ability to generate a digital anatomy of a foot. Such a digital anatomy of the foot includes: (1) the shape and position of the plantar surface of the tarsal and/or metatarsal bones of the foot, (2) a computer generated three-dimensional representation of the shape and position of the bones within the foot, (3) the ability to determine which bones have become displaced from their optimal positions, and/or (4) a three-dimensional representation of joint position and congruency of the foot. A computer software program in the system analyzes the digital anatomy and, based on the analysis, directs the system or a skilled clinician or physician to reposition one or more foot bones, with optional input from the clinician or physician. The digital anatomy of the repositioned foot, with one or more bones in a restored bone state, is obtained, and the digital data file of both the initial and the restored bone states are stored, for use in manufacture of orthoses and/or for subsequent evaluation.

Figure 3A:
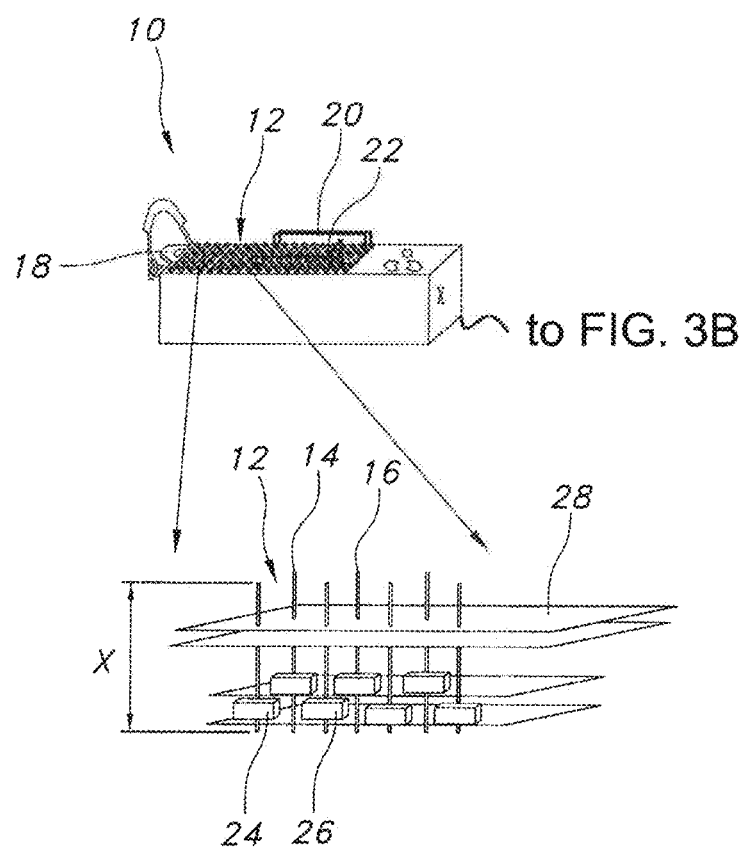
FIG. 3A shows a surface or foot platform, and an exploded view of a portion of the platform, that is a component of a system for use in analysis of a patient's foot and design of an orthotic device.
Figure 3B:
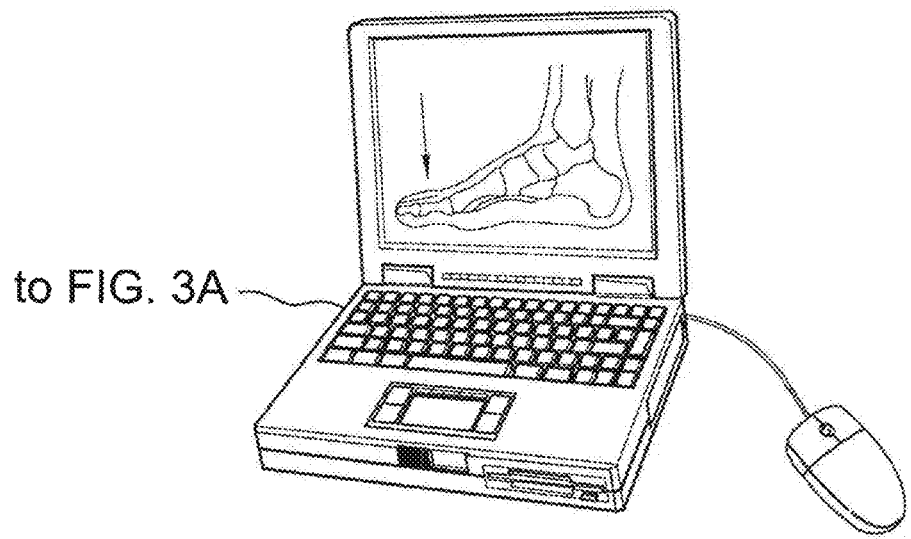
FIG. 3B shows a computer having a graphical display of a patient's foot structure, the computer and its software components of a system for use in analysis of a patient's foot and design of an orthotic device.

FIGS. 3A-3B illustrate components of such a system 10. System 10 comprises a surface 12 for receiving a plantar surface of a foot. Surface 12 is of sufficient size to accommodate measurement of any size foot. In a preferred embodiment, the system additionally comprises a computer (FIG. 3B) with software for analysis and diagnosis, as will be described below. The system optionally includes an imaging system (not shown), also discussed below, for complimentary and enhanced analysis of a foot. The system also comprises a pin matrix, also referred to herein as a pin bed or array of pins, comprised of a plurality of pins that are collectively or, preferably, individually and independently moveable. FIG. 3A includes an exploded view of several pins, pins 14, 16 being representative, in the array of moveable pins. Pin beds are described, for example, in U.S. Pat. Nos. 5,640,779; 4,876,758; 5,941,835; 5,689,446; 4,449,264, incorporated by reference herein. In some embodiments, each pin in the plurality is independently moveable and is under control of a driver, such as drivers 24, 26, coupled to the individual pins to raise each individual pin at a known or controlled pressure. The drivers in the system can be, for example, a piston driven by a pressure source, a serveo-controlled motor adapted to raise an associated pin by a preselected distance, a constant force spring, a hydraulic device, a pneumatic device, or the like. A heel rest 18 can be optionally included at one end of the surface on which the foot contacts. Additionally, surface 12, also referred to as a foot platform, can include stabilizing arms 20, 22 mounted on opposing longitudinal sides of the platform on sliding rails, for application to point-specific areas of a foot at rest on the surface to stabilize the foot and permits its adaptation to feet of varying sizes.

Figure 3C:
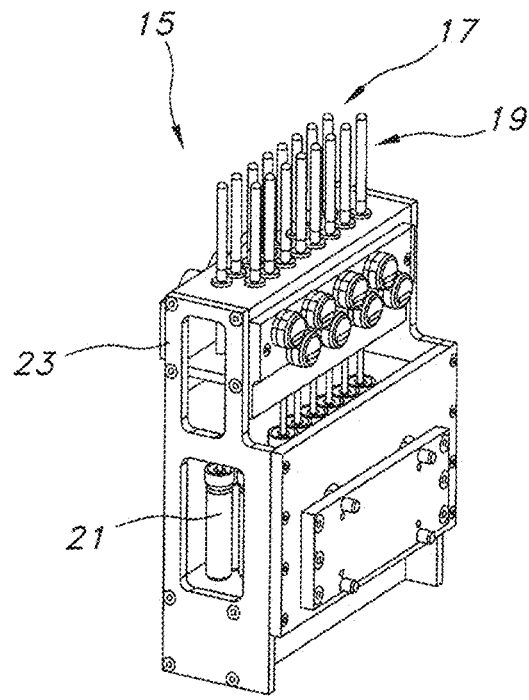
FIG. 3C illustrates an embodiment of a pin matrix for use in the system.

FIG. 3C illustrates an embodiment of a pin matrix. In this embodiment, the pin matrix 15 is comprised of two lateral rows of pins, identified as rows 17, 19. It will be appreciated that two rows is merely exemplary, and that the pin matrix can comprise a single row of pins or more than two rows of pins, such as three lateral rows, four lateral rows, and so on. In one embodiment, the pin matrix comprises from between about one to about four rows of pins. The system includes a plurality of drivers, such as driver 21, coupled to the individual pins. The drivers serve to raise, or lower, each individual pin at a known or controlled pressure. In some embodiments, a common pressure source (not shown in FIG. 3C) is connected to each driver, and in other embodiments, a plurality of pressure sources are provided with at least one pressure source connected to each driver.

The rows of pins, in one embodiment, are held on a carriage 23 that is mounted, for example in system 10 of FIG. 3A, for movement across the surface that receives a patient's foot, such that the pins sequentially engage the foot plantar surface, further described below. The system additionally comprises one or more sensors for determining positional information about the pins in the pin matrix, and in particular for determining a penetration depth of each pin as the pin is raised upward from the surface of the system to engage the foot plantar surface and compress tissue against bones of the foot. In one embodiment, sensors for determining a penetration pressure of each pin as the pin is raised upward from the surface are provided. A controller is preferably connected to the drivers, carriage and sensors, the controller programmed or programmable to sequentially position the carriage incrementally across the foot in an axial direction to scan the entire plantar surface, to raise the pins against the foot tissue at one or more pressures at each sequential carriage position, to collect positional information, such as the depth of pin penetration into the tissue, at each pressure and each incremental position, and/or to control pressure applied to each pin.

In use, the pin matrix in conjunction with the other system components, such as a controller and software, can obtain a digital anatomy of a patient's foot. A patient places his/her foot on the surface of the system. Pressure is applied sequentially to a series of localized regions on the plantar surface of the foot, for example by raising the pins in the pin matrix for contact with the foot and compression of tissue against the foot bones. In the embodiment where the pin matrix is comprised of between about 1-4 rows of pins, such as the embodiment depicted in FIG. 3C, the pin matrix in a first position is used to apply pressure in a first localized region of the plantar surface of the foot, the pin matrix in contact with the plantar foot surface defining a first lateral band of the foot surface. A first set of positional information about the pins in the localized region is obtained. The pressure applied to each pin can be adjusted one or more times to obtain additional positional information of the pins at that localized region. In a preferred embodiment, at least one pressure applied is sufficient to displace one or more bones of the foot to a restored bone state, and positional information when the bones are in the restored bone state. The carriage on which the pin matrix is mounted is then moved sequentially, axially across the plantar foot surface to a second localized region on the plantar surface of the foot, where pressure is again applied to the pins. At each sequential region, or successive lateral band of the plantar surface, in which pressure is applied, positional information of the pins is obtained, from which a digital anatomy, or an orthotic profile, of the foot can be determined.

It will be appreciated that the number of lateral bands of the foot plantar surface depends on the number of rows of pins, the spacing between rows of pins, the size of the patient's foot, and other factors. In one embodiment, pressure is sequentially applied to between about 10-40 successive lateral bands of the plantar foot surface, more preferably 15-35, still more preferably 20-30. Each lateral band, in one embodiment, has a width in the range of about 0.5-4 cm, more preferably 0.5-2 cm. The pressure applied to the individual pins in the matrix can be a common, predetermine pressure or a series of differing common predetermined pressures.

The positional information that is determined allows determination of an orthotic profile. Positional information can comprise, for example, positions of the individual pins at one or more pressures. Based on the positional information of the pins at one or more pressures, an orthotic profile is determined. The profile is used, as described below, to form an orthotic device that achieves a restored bone state. The positional information obtained can also comprise imaging the plantar surface or relationship of one or more foot bones, to construct a digital image of the foot bones. In a preferred embodiment, the positional information is used to determine a therapeutic orthotic profile that compresses tissues sufficiently to reposition bones to a restored bone state.

In one embodiment, consideration of pin density, height, diameter, head shape, operating modes, pin elevation measurement, pin pressure measurement is given. Additionally, software establishing the digital anatomy, heel rest, foot stabilizing assembly, attachment to a computer, and attachment to an imaging system are considered based on the following features.

With respect to density of the pins in the pin bed, the number of pins per square centimeter can be optimized for increased resolution of two- and three-dimensional images. By way of example, pin density can range from about 0.5 pin measurements per $cm^2$ to about 4 pin measurements per $cm^2$, in one embodiment, for scanning of the foot and bone repositioning. The pin density, in one embodiment, is selected to allow the imaging process to gather a sufficient number of data points without the data collection interfering or adversely affecting the data collection/measurement itself in one embodiment, the pins are spaced apart by a distance in the range of about 6 mm to about 13 mm, measured from the longitudinal center line of one pin to the longitudinal center line of an adjacent pin. More preferably, the pins are spaced apart by a distance in the range of about 7 mm to about 10 mm, and in a preferred embodiment, the distance between center lines of adjacent pins is about 8.3 mm (0.325 inch). In a preferred embodiment, the pins are aligned in offsetting rows to accommodate a high density of pins while avoiding the problem of "tenting" in which a pin rises into the pressure well created by an adjacent pin. The diameter of the pressure well is a function of the pin's diameter, the depth of penetration, and the physical properties of the compressed media, such as the skin or soft tissue. In a preferred embodiment, the rows of pins in the matrix are configured in a saw-tooth pattern of between, for example, 1-4 rows, preferably of between about 2-3 rows. The saw-tooth pattern or offset position of the pins is seen in the pin matrix of FIG. 3A and FIG. 3C, where the pins in row 17 (FIG. 3C) are offset from the pins in row 19 (FIG. 3C). These offsetting pin locations are such that as the matrix of pins is moved sequentially to localized regions on the foot surface, the pins in one row when the matrix is in a first position interlace with the pins in another row when the matrix of pins is moved to a second position. The pins are preferably raised simultaneously, but discretely, in each position and information on pressure and pin height is collected in order to determine an orthotic profile or digital anatomy of the foot. The pin matrix when in position at each localized region of the foot may be subjected to more than one pressure, for example, two or three pressures, wherein at least one pressure is sufficient to displace bones of the foot to a restored state. A single row of complete data across the foot is thus collected with 2 or 3 measurements. Effectively, this technique gathers high density pin data across the foot without having any sets of pins too close to one another during any given measurement assuring that the measurement is valid without detrimental effects of "tenting". As noted above, pins are raised into the foot using a driver, such as the drivers identified as 24, 26 in FIG. 3A. It will be appreciated that the drivers can be placed in an alternating pattern and/or on two levels, as shown in the exploded view of FIG. 3A.

With respect to pin height, in one embodiment, the pins have a height, denoted by the distance x in the exploded view of FIG. 3A, of at least about 7.5 cm above a plate 28 on surface 12. This pin height accommodates individuals with a high arch in one or both feet, and permits accurate height readings of each pin. The maximum height of each pin in the array forming the pin bed, in one embodiment, is about 10 cm; and in another embodiment is about 11 cm, 12 cm, 13 cm, or 14 cm.

Diameter of the pins is ascertained upon consideration of a balance of at least two parameters: the pins should be of sufficient diameter to compress tissue effectively without causing pain, yet small enough to prevent pressure well overlap of adjacent pins. In some embodiments, pin diameter is small enough to provide as many points of reference as possible and yet thick enough to bear the weight of a heavy human (up to 400 lbs.) standing on the machine. In some embodiments, the plurality of pins can be arranged in a repeating hexagonal pattern to minimize spacing between the pins. In some embodiments, a 50% offset between rows of pins is envisaged. In some embodiments, an offset triangular grid may allow greater density of pin placement, as well as increased accuracy in a high-contour plot.

In some embodiments, the pins may have a circular cross section. The pin head surfaces can be smooth and slightly convex in shape to evenly distribute forces over the entire pin head surface.

Figure 3D:
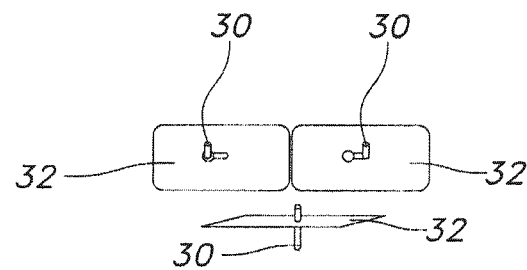
FIG. 3D illustrates a pin in an array of moveable pins, and a locking mechanism to secure the pin in one embodiment.
Figure 3E:
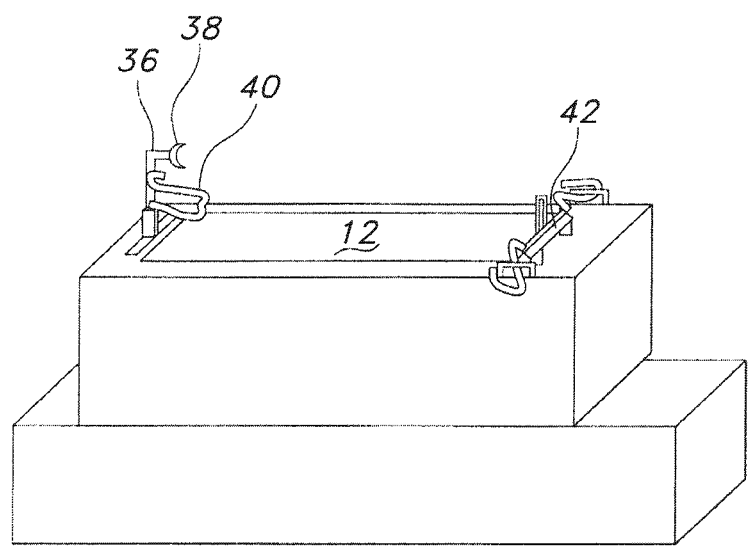
FIG. 3E depicts a heel rest assembly to assist in positioning a foot on a pin bed to obtain a digital anatomy.

In use, a patient places his/her foot upon the pin bed. The system applies a selected pressure to the pins, the pressure applied being sufficient to compress the soft tissue on the plantar surface of the foot to create a uniform density of tissue per cubic centimeter at each pin head surface. Thus, rather than passively receiving pressure from the foot and settling into a position based on the topography of a patient's foot, the presently disclosed pin bed or band of pins can actively control the pressure of individual pins. In one embodiment, several phases of pressure can be applied until a desired pressure is reached. Pin pressures can be monitored to assure that the same pressure is delivered to each pin. As can be appreciated, pin heights increase until the pressure against each pin by the foot equals the pressure exerted by each elevated pin. When the two pressures are equal, pin elevation stops and the pins can be measured for pin height and pressure. A digital anatomy of the foot is created based on the position of each of one or more pins and the applied pressure, and the image of the anatomy is digitally stored. Creation and analysis of the digital anatomy is described below. In one embodiment, after analysis of the digital anatomy, and with the patient's foot in place on the pin bed, selected pins in the array of pins in the bed are adjusted in an upward or downward position to adjust and/or reposition selected bones in the foot, to restore a desired or proper bone position, and tensegrity structure of the body in one embodiment, as determined by the computer software. In this adjusted position, the pins are now aligned to mimic the shape of a custom orthotic and to allow the patient to sample their orthotic prior to its manufacture. After the bones have been repositioned by the pins, another digital anatomy of the restored foot may be created. Though the preferred embodiment does not utilize a locking mechanism or pre-manufacture comfort testing, in one embodiment the pins can be locked in place using a locking mechanism illustrated in FIG. 3D. In FIG. 3D, a pin 30 extends through a foot plate 32, as seen best in the lower panel of FIG. 3D. Pin 30 in its unlocked position is shown in the left panel of FIG. 3D, and it is locked position in the right panel of FIG. 3D. In the embodiment utilizing a pin locking mechanism, the patient can stand on the instrument whose pins are locked to test the approximate shape of the final orthotic for comfort prior to its manufacture.

In cases requiring a correction to pin heights that are too large to achieve the desired restored bone state in a single orthotic device, a series of two or more orthoses are designed where the computer defines the shape and contour of the orthoses to progressively move the bones to the restored bone state.

In one embodiment, the pins in the array of pins in the bed are elevated individually by applying pressure to each pin simultaneously and within certain tolerances. The height of each pin can be individually monitored and controlled by computer. Pressure regulation can be controlled by the software yet will also allow for manual adjustment by the practitioner. In other embodiments, pin elevation is optically monitored for each pin by the computer software, and in some embodiments pin height accuracy will be assured to within 0.05 mm or better. As is evident from the description above, pin elevations can be measured several times during the analysis and diagnosis of a patient's foot. An initial pin elevation measurement is taken when the pins are in full contact, low compression against the plantar surface of the foot in order to achieve a baseline static structural image. After the pins are in full contact with the patient's foot at low compression, the pressure is then increased, compressing tissue to a uniform density, and the pin elevation measurement is (again) taken. The step of increasing pin pressure measuring pin elevation is repeated a number of times, resulting in a series of digital anatomies of the foot. Additional adjustments to the bones may be made by the computer via pin elevation or manually by the practitioner in order to achieve an optimal restored state. In this way, baseline and corrected images of the foot are documented.

A range of forces between 0 and 50 Newtons can be applied to the pins, and applications of force can occur iteratively. Pin forces will typically be in a range from 0 to 5 lbs (0 to 30 N) per pin. A typical pin diameter is from about 0.10 to 0.25 inch (2.5 mm to 6.4 mm).

A heel rest on the foot platform can be included, as illustrated in FIG. 3D, to maintain proper shank position. The heel rest can include a removable or foldable curved bar 36 that stabilizes the heel and lower leg and minimizes their movement or slippage, yet allows pins to elevate around the heel area to capture the natural shape. In addition, a curved bar 38 continues past the level of the ankle malleoli and has an adjustable strap 40 that is positionable about the ankle for better stabilization in those instances where hypomobility would normally require two people to position the foot for scanning. This bar, in one embodiment, would have a variable angle to the foot platform with a "normal" notch set at 110 degrees. For most patients this angle will take tension off of the calf muscles and prevent activation of the tensile components of the foot including the LCNC complex and the intertarsal ligament complex while still maintaining proper contact with the foot platform.

In addition to the heel rest, the foot platform can additionally include a foot stabilizing assembly 42 to hold steady the first and fifth metatarsal heads so that the tensile elements are not under tension and therefore the LCNC complex and internal tarsal ligaments are not activated. The foot stabilizing assembly includes a strap that can be adjusted and fastened in place, using conventional fasteners such as, but not limited to, buckles, hooks, Velcro, loops, or other types of fasteners. The foot stabilizing straps are anchored on movable rails so that any size foot can be accommodated. Under the strap, two elastic pieces (for example rubber or rubber-like pieces) are placed over the first and fifth metatarsophalangeal (M-P) joints so that the pressure created by the strap applies pressure only over those two joints. The two rubber pieces are shaped to fit smoothly over the first and fifth M-P joints and are attached to the strap in such a way as to allow them to move along the length of the strap, and are therefore adjustable to any size foot. The foot stabilizing assembly may also incorporate a tensioning element (such as a spring) that applies a force towards the heel of the foot so that as the pins raise the bones of the midfoot, increasing the height of the medial and lateral arch and reducing the length of the foot, the foot stabilizing assembly moves toward the heel to accommodate the foot shortening. The foot stabilizing assembly may also incorporate a ratchet mechanism that prevents the foot from lengthening after the pin pressure under the midfoot is released.

With reference again to FIG. 3A, the foot platform is in communication with a computer and its software, the communication via, for example, ports and cables or a wireless arrangement. The computer may also be linked to an optional imaging system, described below, also by ports and cables or wirelessly, unless the particular imaging system requires a special connection.

Turning now to the software that accompanies the system, the software acquires pin height data along with stored information of a generalized skeleton of the foot to form a three-dimensional representation of the particular skeletal and soft tissue anatomy of the patient's foot. Pin height varies depending upon the thickness and density of soft tissue between the plantar surface of the foot and the underlying bone. The soft tissue beneath weight-bearing bone, such as at the tubercle of the calcaneus and under the first and fifth metatarsal heads, will be higher in density and harder to compress, resulting in minimal pin elevation. In areas where bones are deeper to the plantar surface, soft tissue may be thicker and will have a lower density allowing it to compress more under the same pressure. In those areas the pins will elevate more to reach pressure equilibrium. The software captures the elevation of each pin once a uniform density of the foot structures is achieved.

Characteristics of the presently disclosed software are: (i) it enables data gathering from pins' pressures and elevations to display graphic representations of various aspects of the foot; (ii) it provides viewing of certain images from any angle; (iii) it contains rules for displaying the digital anatomy of the foot in two- and three-dimensional representations, for example, by showing a congruency map optionally allowing the visualization of articular surfaces of the bone(s), or by showing a vector map allowing visualization of the bones to be manipulated, wherein the congruency or vector map can change upon pin adjustment or human manipulation techniques; (iv) it contains rules for diagnosing structural abnormalities of the foot, for example by detecting one or more bone alignments and drawing lines 1-4 (as described in Example 2), assessing misalignment(s), and suggesting movements of one or more bones to achieve a desired angle and/or to establish congruency; (v) it contains rules for restoring proper bone alignment without overcorrection and automatically detecting and updating the alignments and redrawing lines (for example, to superimpose lines 1, 2 and 3, optionally based on a minimum movements criterion, and to allow the intersection of lines superimposed 1-3 with line 4 at approximately a 90° (+/−3°) angle, as described in Example 2); (vi) it contains rules for determining, at the diagnostic phase, when serial orthoses are needed (such as when the elevation of pins for moving bones within a patient's foot generates intolerable discomfort for the patient, and/or such that no ligament is stretched beyond a certain percentage of its original length, even if the patient feels no discomfort), and recording the corresponding distances from initial untreated bone position to the desired and/or prescribed restored bone position(s), and computing and/or dividing those distances into intermediate segments/steps for determining a series of intermediate bone repositionings needed and designing a series of more comfortable progressive orthoses, thereby determining the shape of each orthosis the series; (vii) it transfers the data for the restored foot to an orthoses manufacturing instrument; (viii) it will determine how much correction can be performed comfortably for each patient based on information gathered from the diagnostic mode; (ix) it is able to quantify the relationship between the bones of the foot and quantify their respective movements in order to give practitioners guidance and enhance individual patient treatment; and/or (x) it can provide a quantitative digital display of the bones' positions.

The computer software provides a three-dimensional rendering of the compressed soft tissue of the plantar aspect of the foot at uniform soft tissue density, and an overlay of more than one of such three-dimensional displays under different compression pressures. To provide this rendering, the computer software can simulate the anatomy of the patient's foot, or of a restored foot, using, for example, a colored representation of the topography of the compressed tissue based on analysis of pin heights. The software can also identify the long axis of any bone, annotate the display, and/or prescribe and/or adjust pin height needed to move one or more bones of bone movement in six degrees of freedom to a restored position. The software can display the prescribed orthotic designed by the system.

The software provides, in some embodiments, the following types of graphic representations of the foot measurements. In one embodiment, a three-dimensional color-coded computer simulation of the patient's foot skeleton showing bone alignment and joints based upon calculations made by the software based upon pin height data is provided. In another embodiment, a three-dimensional "wireframe" rendering of the compressed soft tissue of the plantar aspect of the foot at uniform soft tissue density is provided. In another embodiment, a customized three-dimensional skeletal representation of the patient's foot incorporating all data of the digital anatomy into a computer simulation of the foot skeleton is provided.

The three-dimensional simulation can be rotatable for full 360° viewing in all three planes by using a mouse or roller ball pointing device, allowing the practitioner to view the skeletal representation of the foot from any angle and vantage point.

The software can move some or all of the virtual bones of the digital anatomy as would occur in an actual foot whenever the practitioner makes an adjustment by moving a single bone. In other words, when the practitioner makes a single adjustment on the computer, the rest of the bones of the foot move in response, as they would be predicted to move in nature.

Analysis and Diagnosis

Figure 4A:
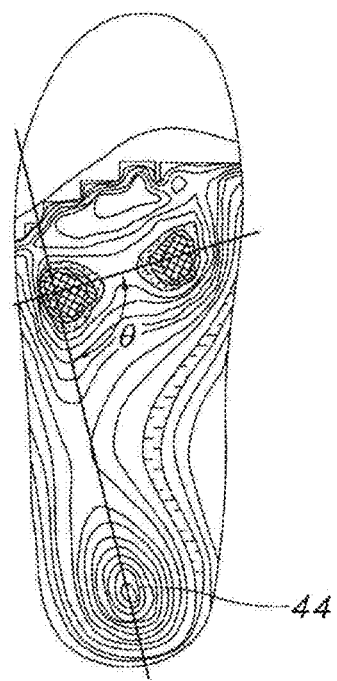
FIGS. 4A-4B provide graphic representations of two views of a digital anatomy of a foot.
Figure 4B:
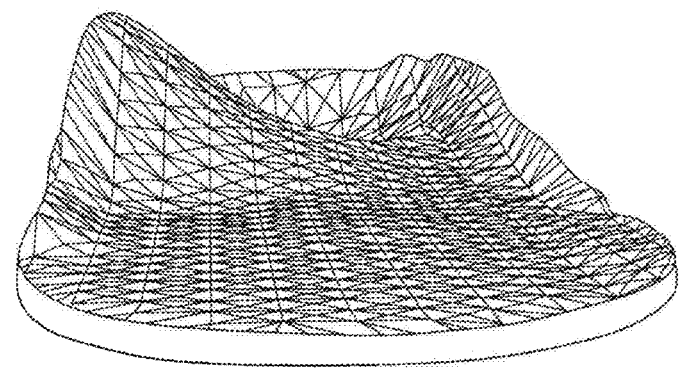

After measurement of a patient's foot by placement on the foot platform and movement of the pins to compress the soft tissue on the plantar surface of the foot to create a uniform density of tissue per cubic centimeter at each pin head surface, the computer program analyzes the collected pin height data to determine bone positions of the foot, first assessing the shape of the inferior surface of the calcaneus. As shown in FIG. 4A, which represents a contour plot of the compressed soft tissue of the plantar surface of a foot, ascertained by the computer software based upon pin height, the ideal appearance of the shape of the inferior surface of the calcaneus is circular shape, indicated at 44. If the calcaneus is not in an ideal position, the shape will appear as an oval indicating that the calcaneus is plantar flexed, as visible in the contour plot of the foot in FIG. 5A and identified at 46. The computer then uses this data to conduct an analysis of the foot, using various techniques, one of which is detailed in Example 2 with reference to FIGS. 6A-6F.

In some embodiments, an additional function of the computer includes measurement and analysis of a patient's uncorrected, unmanipulated foot on the pin bed. At the same time, the first and fifth metatarsal heads are held to the pin bed surface still allowing for movement of the rest of the forefoot. The computer then sends a signal(s) to the pins in specific areas for which a bone adjustment to achieve restoration is desired, to apply one or more thrusts of fixed or increasing pressure for active repositioning of bone and restoration of foot physiology. The thrusts may be repeated several times at the clinician's discretion. Variable amounts of such active repositioning and restoration will be achieved. The clinician stops this process when he or she determines that no further restoration or repositioning can be achieved or tolerated. A static digital anatomy is then obtained. Thus, the system itself can be a device actively involved in a treatment plan to supplement or in place of manual manipulation.

As mentioned above, the system can optionally include an imaging system. An imaging system allows the visualization and display of a virtual representation of the positions of the bones and joint spaces in the foot. The imaging data that is gathered can be digitized, stored and added to the data captured from the pin bed to further refine the three-dimensional computer graphic simulation of the foot skeleton. This enables the examining clinician to visualize abnormal bone position in a more detailed manner and to use the system to make the desired adjustments to the bones of the foot that will restore it to a more ideal or normal structure and function. Some examples of means of imaging include, but are not limited to ultrasound; an MRI, such as a portable MRI; x-ray, CT scanning or infrared imaging.

In some embodiments, the system additionally comprises an ultrasound imaging device. In some embodiments, a four-dimensional ultrasound device is included that permits visual representation in real time using a combination of ultrasound data along with a computer program that yields a simulation viewable on a color monitor. When combined with the present system a four-dimensional ultrasound of the foot in combination with pin position data and a computer model of a foot skeleton, a virtual representation of the bones of a patient's foot can be obtained, as illustrated in FIG. 3B. In this system, the practitioner need not be trained to read ultrasounds. Practitioner training can be centered on comprehension and interpretation of a patient's digital anatomy, the relative bone positions and the appearance of an ideal or restored foot.

FIGS. 4-8 illustrate use of a digital anatomy obtained using the system for identification of foot pathologies, and ultimate design of a restorative orthosis. FIG. 4A shows a two-dimensional topographical image and FIG. 4B shows a three-dimensional wireframe image of the foot. The topographical map is delineated in millimeter increments, with the cross-hatched area demonstrating no elevation of the pins, the shaded area approximately 1 mm, the stippled area another millimeter, and subsequent lines denoting further or different pin elevations. A foot that is distributing weight properly will carry approximately 50% of the weight on the calcaneus, about 25% the weight will be carried on the first ray, and the rest will be evenly distributed over toes 2 through 5. The two-dimensional scan shows that pressure can be related to topography in that the area of the greatest pressure will be less likely to deform under the pin pressure. Therefore, in FIGS. 4A and 4B, the area with the least pin elevation (the area bearing most weight) is over the first, fourth, and fifth metatarsal heads.

Figure 5A:
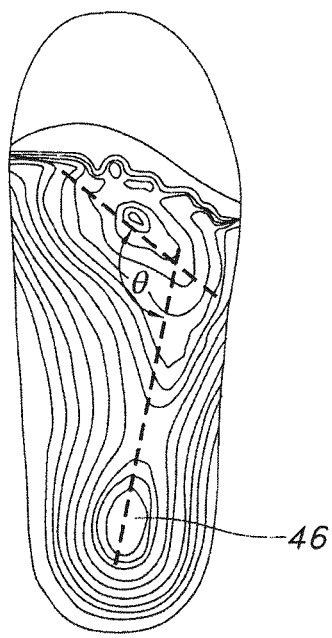
FIGS. 5A-5B provide a graph representations of two views of digital anatomy of an abnormal foot.
Figure 5B:
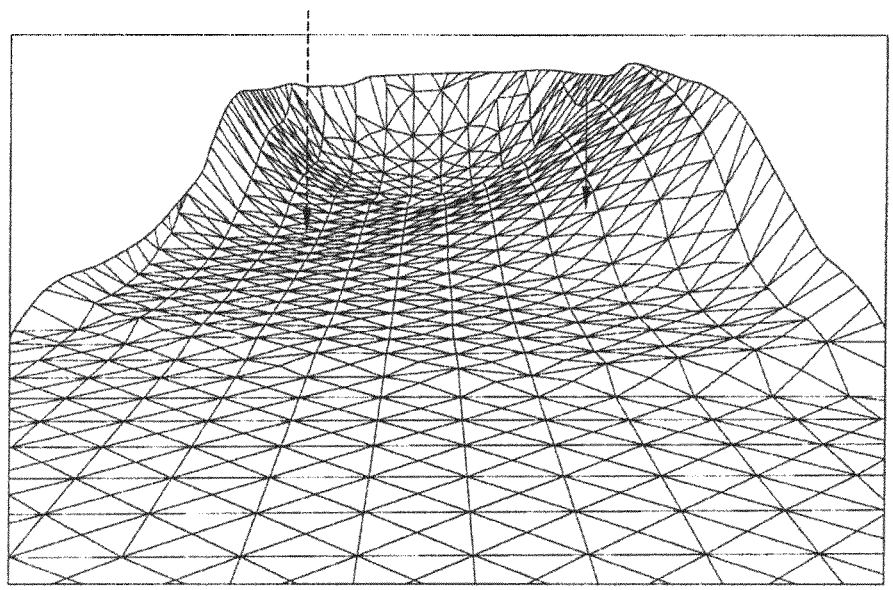

In FIG. 5A, an image of an abnormal foot bone structure, the area of least pin elevation (the area bearing the most weight) is in the middle of the forefoot, right over the third metatarsal head. In this case, the third metatarsal head has dropped, the medial and lateral metatarsals have elevated, or there is a combination of both. Looking at the three-dimensional wireframe image, it can be seen that the medial arch is very high (solid arrow), while the lateral arch is very low (dashed arrow). Since there is a small lateral arch, the cuboid has not completely collapsed as it is the apex of the lateral arch triangle (identified by the dashed arrow). Therefore, the foot in FIGS. 5A-5B represents a combination of collapse of the mid-foot, dropping the third metatarsal down, along with elevation of the medial and lateral elements. Both the tarsal and metatarsal transverse arches are essentially inverting and becoming "V" shaped because the lateral cuneiform, navicular, cuboid (LCNC) complex has failed, preventing the medial and lateral columns to join together as a single, functional unit during specific phases of gait. The LCNC complex is shown in the X-ray of FIG. 7. The cuboid is marked with a "C," the navicular marked with an "N," and the lateral cuneiform is marked "LC." In the foot shown in FIGS. 5A-5B, the LCNC ligamentous complex has failed, and the two ideally weight-bearing portions of the forefoot (the first metatarsal and fifth metatarsal) have given way, resulting in the transverse metatarsal arch becoming convex in shape rather than concave with the third metatarsal head now against the ground and bearing weight.

Figure 7:
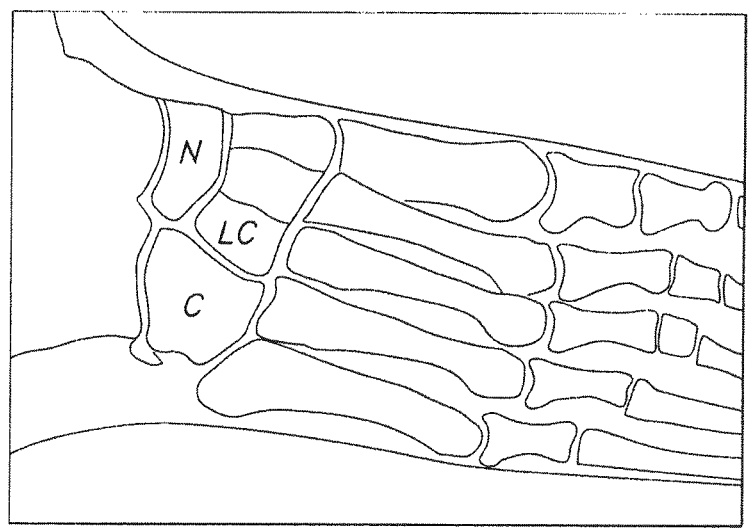
FIG. 7 is a computer-generated image of an x-ray of a foot, with the hones of the lateral cuneiform-navicular-cuboid (LCNC) complex labeled.
Figure 8A:
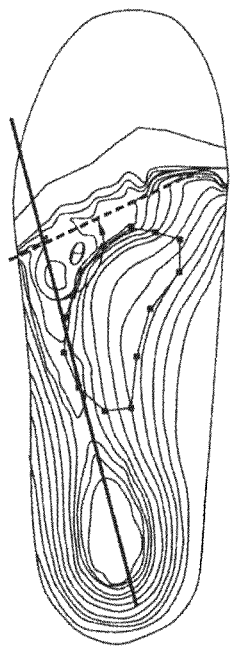
FIGS. 8A-8B are graphic representations of two views of digital anatomy of an abnormal foot.
Figure 8B:
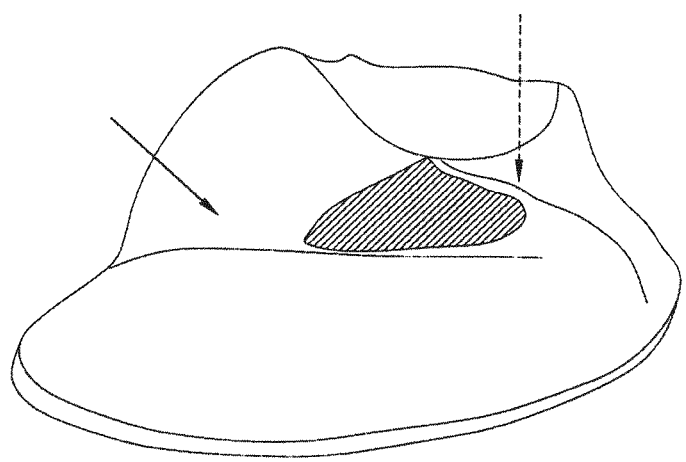

FIGS. 7-8 are examples of digital images of exemplary feet having a malposition of the calcaneus. FIG. 8A shows a digital image of a foot, where a series of reduction lines are drawn for analysis of the foot structures. A reduction line is drawn through the transverse metatarsal (dotted line), and reduction lines drawn through the long axis of the calcaneus, the bisection line of the cuboid and the line between the fourth and fifth rays are all overlapping (solid line), indicating that the calcaneocuboid joint is congruent in the frontal plane. The angle "theta" between the dotted line and the overlapping solid lines is close to the ideal of 90 degrees indicating that the transverse metatarsal arch is approximately normal. Though it is congruent in the frontal plane, the calcaneocuboid joint is not congruent in the sagittal plane because instead of having a circular shape as expected from the circular tubercle of the calcaneus, this case has a long ovoid shape. FIG. 8B shows that the lateral column in this foot is flat. It also shows a depression beneath the dashed arrow where the cuboid has been forced downward by the plantar flexed calcaneus. The flat lateral column such as in FIG. 8B is observed in patients who have congenital pes planus. However, the foot in this figure also shows an ovoid shape to the calcaneus indicating that it is abnormally plantar flexed and that the flat lateral column is both abnormal and not congenital. This figure illustrates a classic presentation for a functional short leg.

Figure 9A:
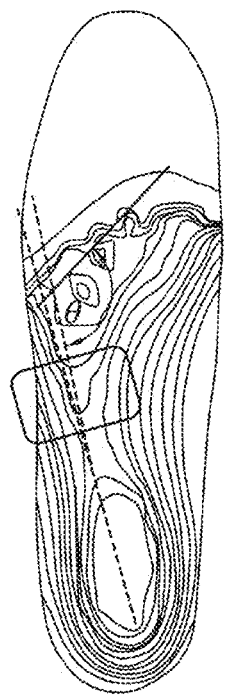
FIGS. 9A-9B are graphic representations in two views of digital anatomy of an abnormal foot.
Figure 9B:
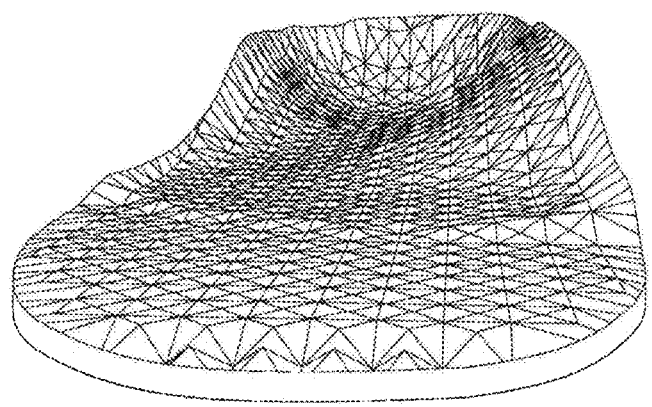

FIGS. 9A-9B also illustrate a foot having an ovoid shape of a plantar flexed calcaneus, but in this ease it is indicative of a functional long leg. The area delineated by the rectangle shows the subtle shift in the direction of the calcaneus versus the direction of the fourth and fifth ray. The dotted lines show the lateral column and calcaneus reduction lines. In an ideal foot, these would overlap, but in this case they do not and their offset angle meets at the cuboid indicating that the calcaneocuboid joint is no longer congruent. Also, the transverse metatarsal line (solid line in FIG. 9A) makes a theta angle much greater than 90 degrees, indicating that this foot has broken down in several areas. The 3-dimensional image (FIG. 9B) shows that all three arches are decreased and that the lateral column is very flat.

The computer program of the presently described system performs the above analysis and suggests a diagnosis or a differential diagnosis for each patient. The program then prescribes treatment options for practitioners who wish to manipulate the bones of the foot prior to application of an orthosis for restoration of structure and function to the foot and fabricate the orthosis in-office, as well as for those who wish to have the orthosis or series of orthoses in a treatment plan fabricated at another location using this system.

Restoration Based on the Analysis and Diagnosis

To restore the foot to an optimal bone state, the system described above identifies the joints in the foot whose tensile structures have undergone plastic deformation and then manipulates the foot in silico, or manually, to bring them into congruency.

To achieve this, the patient's foot is placed on the foot platform of the system, a digital anatomy is obtained, in one embodiment with the pins of the pin bed adjusted to manipulate the foot into its restored bone state. This digital anatomy is referred to herein as the "restorative digital anatomy." In some embodiments, the patient's foot has been manually restored prior to obtaining the restorative digital anatomy. From the restorative digital anatomy, the system performs an additional set of calculations, similar to that described above, and moves the pins into a position to achieve a restored bone state. In one embodiment the pins can be locked in place, and the pin positions represent the shape/contour of the orthotic to be fabricated. The patient can stand on the pin bed to assess comfort, and minor adjustments may be made by the practitioner as needed for comfort or to improve congruency between one or more foot structures. After any adjustments to the pins, they are once again locked, the position of the pins evaluated by the software, and the data stored for subsequent analysis or fabrication of an orthotic device.

It will be appreciated that while the description of the method and system set forth above is illustrated using a pin bed for obtaining a foot digital anatomy, the method and system are not limited to a pin bed alone to obtain a digital anatomy. Imaging techniques are also contemplated and would be suitable in supplementing the data from the pin bed in constructing the digital anatomy.

The method described herein contemplates serial orthoses in a treatment plan, in which one or more intermediate orthoses are designed to move the bones from an initial bone state to a restored bone state. Such a series of gradually more corrective orthoses moves and stretches soft tissues, to move the pathologically positioned bones of the foot into restored positions. A patient will wear the first orthotic device in the series for a first period of time selected by the clinician, typically on the order of several weeks or months. Then, the patient wears the second and any subsequent orthotic devices in the series for a selected period of time, which can be the same or different than the period of time for the first orthotic device. The sequence continues until the patient is wearing the final orthotic device that accomplishes a restored bone state.

Another means of effecting restoration is for the system to be modified to automatically manipulate the foot in place of the practitioner. This can be accomplished using one or both of the following methods. First, with the foot secured to the pin bed and under minimal weight bearing with the patient seated, high velocity, low amplitude thrusts in an upward direction are made by pins or groups of pins as determined by the accompanying software. Second, as the pins are advanced slowly toward the accompanying software determined restoration position, they are oscillated (or vibrated) rapidly in an up and down direction while the foot is secured by the retaining device and under minimal seated weight bearing. Both of these methods can be combined where the pins oscillate rapidly up and down and selected pins or groups of pins make periodic high velocity, low amplitude thrusts in an upward direction until restoration is acquired. As a safety measure, the system can optionally continue to monitor pin pressure and can stop pin advancement should a predetermined pressure be exceeded.

C. Manufacture of an Orthotic Device

Figure 11:
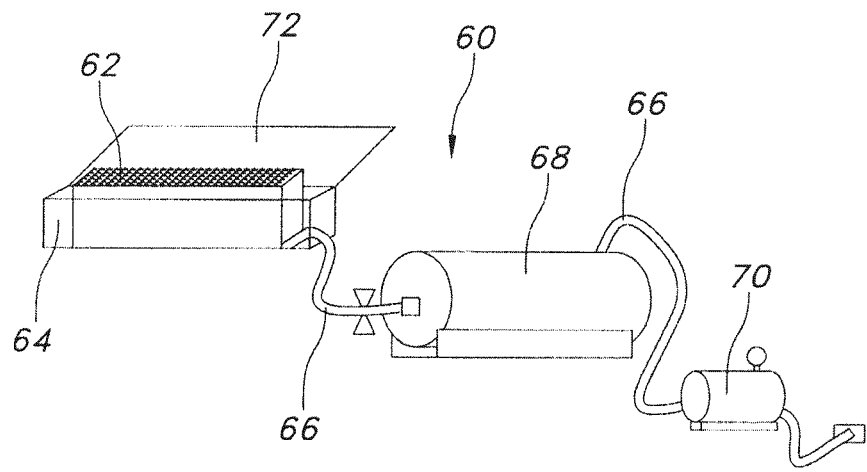
FIG. 11 is an illustration of components of an orthotic manufacturing system.

In another aspect, the system further comprises an instrument for the manufacture of one or more restorative foot orthoses. FIG. 11 illustrates an embodiment of a manufacturing instrument for use with the system. In the example, the manufacturing instrument 60 includes a pin bed 62. The pin bed sits within a vacuum chamber box 64, and extends approximately two inches above the rim of the vacuum chamber box. The vacuum chamber box is attached, via a hose 66, to an evacuation chamber 68 that has double the volume of the vacuum box chamber. The evacuation chamber is connected to a vacuum pump 70. In some embodiments, the hose and opening in the chamber will be sufficiently large enough to evacuate the entire chamber in less than three seconds. The vacuum chamber box can have a hinged cover with an aluminum frame with heavy heat resistant rubber screwed to it for easy replacement, to provide an airtight seal when closed.

The pins of the pin bed are covered by a material 72 that serves to prevent the pin heads from pitting the finished product. The pins are moved into the desired position, determined from the measuring and analysis described above to move a patient's foot into a restored bone state. A blank insert, i.e., a flat sheet of a selected material(s) to make the orthotic, is heated to a temperature sufficient to render it pliable for forming into the shape of the custom orthotic. The blank insert is positioned over material 72, and the vacuum box chamber in which the pin bed is position is closed. A rapidly produced vacuum, via pump 70 in communication with vacuum chamber 68, is applied to shape the orthotic device.

After cooling, the orthotic is removed from the pin bed and the edges are smoothed, for example, using a carbide wheel.

The orthotic device is manufactured, in another embodiment, using pressure forming. A pressure former is comprised of two clam shelf boxes arranged such that the top half pressure box is comprised of a five-sided box with an opening on the sixth side. This sixth side is covered with a rubber-like or elastic membrane and sealed to the rim of the box. This box is brought down onto another box frame of the same perimeter which has its sixth side open and facing up to meet the rubber-like membrane. Inside the second box, the mold shape is positioned in its cavity. A heated and pliable orthotic material is placed over the mold. The two box halves are then brought together and held tight with clamps. High pressure air is released into the top box half into the cavity volume that is sealed with the rubber membrane. As the pressure builds in this cavity, the rubber-like member stretches down onto the waiting orthotic material and forms it to the mold shape which it is resting on. The rubber-like member stretches sufficiently to force the orthotic material to take the identical shape of the mold. The pressure is held for a few minutes until the orthotic material's temperature drops below its glass transition temperature. At this time, the pressure in the upper cavity is released, the two halves of the fixture are separated, and the molded orthotic shape is removed from the mold. Pressures in the forming cavity used typically range from 0 to 6 bar (0 to 90 psi).

In another embodiment, the orthotic device is manufactured by milling from a positive foam mold. The process of producing the foam mold is done by milling it using a milling machine. The data set is derived from the measured data, discussed above, and manipulated appropriately. This file is then converted into tooling paths which in turn drives the mill. The final foam shape is the shape either the inside or the outside of the desired orthotic shape. Tapers, bevels and other features are inserted outside of the data that represents the final shape of the orthotic that bridge the mold to a base so that the mold can be positioned and held appropriately in the pressure or vacuum forming tools.

In another embodiment, the orthotic is manufactured using the pin bed of the device. In this embodiment, the computer software of the system retrieves the data used in the measuring and analysis of the digital anatomy to reproduce the identical pin configuration for manufacture of the orthosis, except that it is converted to a positive image. For example, the locked gauging elements of a pin bed can provide a form to serve as a positive mold for fabricating an orthotic. In other words, it will assume the shape of the bottom of the foot with the restoration. Data for a particular patient is sent from the computer in the system described above to the pin box in the manufacturing unit, and the pins rise to the patient specific, restored shape. The already heated orthotic blank is then seated on the pin bed.

Once the presently disclosed orthotic has been constructed, it can then be sandwiched between two covering materials, in one embodiment, before proceeding to packaging and shipping. These coverings can be individualized to the patient's tastes and needs. For example, a top covering of the neoprene product identified by the tradename Neolon® (Medline industries, Inc.) enhances patient comfort and helps keep the foot well seated. Furthermore, a leather bottom enhances the fit of the orthotic in the shoe and minimizes movement of the orthotic within the shoe. Finally, both layers uniformly increase the post of the orthosis within the shoe. It should be noted that alternative top layers may be used in special situations. A top covering of, for example a closed foam polyethylene, such as Plastizote® (Zotefoams, Inc), provides cushioning and is bacteriostatic, which may be suited for particular patients or conditions. In another example, women using the orthotic primarily in dress shoes may prefer a top layer that is also made of leather that is thin and also helps keep the foot in place within the shoe. Other orthotic top and bottom coverings may be used as they do not affect the structure and function of the device itself.

Materials suitable for forming an orthotic device are known in the art. In general, materials that form orthotic devices with one or more of the following properties are suitable: (i) energy storage and return, (ii) thermoplastic that is easily molded under heat and vacuum, (iii) a tensegrity weave and aramid to prevent fracture, (iv) small load range (movement from zero to full capacity), and (v) skid resistant undersurface minimize insert movement within the shoe. Common materials include ethyl vinyl acetate (EVA), which comes in various durometers, and polymer plastics such as polyethylene, polypropylene, or co-polymer plastics.

In some embodiments, an orthotic is made of a carbon and aramid tensegrity weave, optionally impregnated with acrylic and a plasticizer. Because aramid fibers have a short "toe region" like collagen (as seen in FIG. 1), appliances manufactured from an aramid fiber, such as a bullet-proof vest, effectively and rapidly absorb and dissipate force, such as force of a bullet. Graphite, which is more commonly used alone in rigid orthoses, dissipates energy to a significantly lesser degree. In another embodiment, a combination of two materials is used, providing an orthotic material which stores and returns energy (like graphite) and also prevents fracture (like aramid) when greatly stressed. A carbon-aramid weave can be impregnated with a thermoplastic, conveying the ability to create blanks and heat-vacuum mold them into customized orthotics. One suitable thermoplastic is a semi-crystalline thermoplastic, conveying the ability to flex and return to its formed shape many times before cracking.

Figure 10:
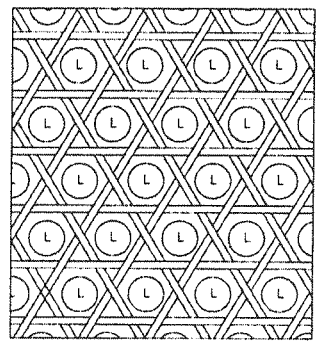
FIG. 10 is an illustration of a Left-Hand Tensegrity Weave.

The weave of the carbon and aramid is preferably loose enough to change its conformation within the thermoplastic so that it can form the radii that control osseous position, yet it maintains a tensegrity conformation, as illustrated in FIG. 10, to withstand the stresses of gait, especially running. A tensegrity weave impregnated with a thermoplastic of an appropriate ratio of acrylic to plasticizer gives both the required energy storage and energy returns within prescribed temporal limits. The presently disclosed orthotic materials provide energy storage and return within a narrow range of time such that the arches of the foot and the intercuneiform linkage can function yet not collapse as did its previously supportive tensile structures of ligaments, tendons and fascia.

In another aspect, an orthotic device is provided. The device is preferably designed according to the methods described herein, and/or the system described herein. The orthotic device preferably has a minimum of three layers: a top and bottom cover and a custom molded center. An exemplary orthosis 130 is illustrated in FIGS. 13A-13C. With initial reference to FIG. 13A, the medial and lateral sides of the device are indicated at 132, 134, respectively. The proximal end, where the calcaneus bone, or heel, of the foot sits, is indicated at 136, and the distal end is indicated at 138. As best seen in FIG. 13B, where a skeleton of a foot is shown placed on the exemplary orthotic device, the orthotic device is sized such that the distal end terminates approximately at the metatarsophalangeal joints of the foot, indicated at 144. That is, the custom molded center layer is sized to extend from the proximal end of the foot (e.g., the proximal surface of the heel) to a terminus defined by a line running approximately ⅓ of the metatarsal's length proximal to the first metatarsal head, just proximal to the second, third and fourth metatarsal heads tapering back so it is approximately ⅓ of the metatarsal's length proximal to the fifth metatarsal head producing a support for the transverse metatarsal arch. It will be appreciated that in other embodiments, the device can be sized to extend from the proximal end of the foot to contact all or a portion of the phalanges.

With reference again to FIG. 13A, arrow 140 designates a line drawn on the orthotic device that denotes the region and contour of the orthotic device that is referred herein as the "saddle" of the orthotic and identified by arrow 146. This area is custom molded to reduce or eliminate any abnormal plantar tilt of the calcaneus, i.e. control the calcaneus in the sagittal plane. This is needed because the calcaneus plantar flexes as plastic deformation occurs in the long and short plantar ligaments causing incongruency of the calcaneocuboid joint with that joint space widening along its plantar surface. When the calcaneus is lifted back to its correct position, the calcaneocuboid joint's congruency is restored. Also seen in FIG. 13A is a marked region 142 that is referred to herein as the "LCNC Dynamic Post". The LCNC Dynamic Post region of the device is a convex area, with the base of it defined by four points, designated as 1, 2, 3, 4, in FIG. 13A: 1) the most inferior part of the head of the first metatarsal, 2) a calculated point between the most inferior parts of the fourth and fifth metatarsal heads, 3) the most inferior point of the lateral side of the calcaneocuboid joint, and 4) the most inferior point of the medial side of the calcaneocuboid joint. The apex of the LCNC Dynamic Post is defined by the highest point on the undersurface of the second metatarsal, which lies about one third of the way proximal to the second metatarsal head. It will be appreciated that the LCNC Dynamic Post varies in size depending on the patient. In FIG. 13B, it is seen that the saddle 146 is under the transverse tarsal arch and the LCNC Dynamic Post is under the metatarsals (arrow 148).

Figure 12:
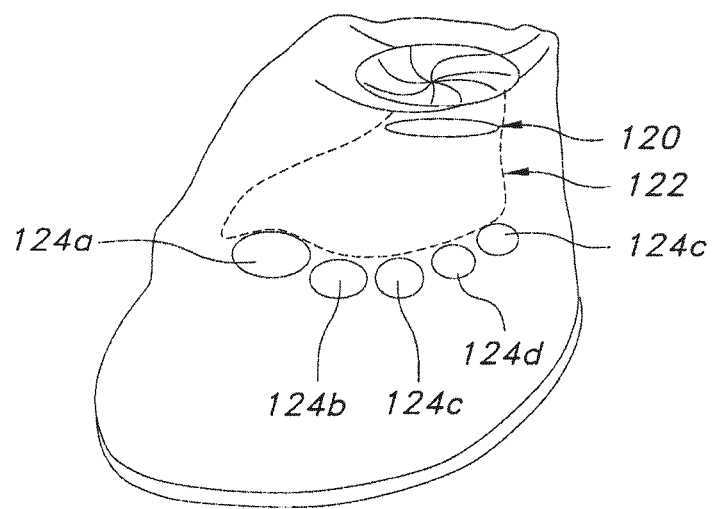
FIG. 12 illustrates a LCNC Dynamic Post.

Based on the foregoing, and in particular with respect to FIG. 12 and FIGS. 13A-13B, it can be appreciated that the orthotic device contemplated herein is, in one embodiment, shaped and/or contoured to comprise a convexity herein referred to as the LCNC Dynamic Post (see region denoted by the dashed line indicated by arrow 120 in FIG. 12), such that the convexity supports at least the Lateral Cuneiform, Navicular and Cuboid bones, i.e. the LCNC complex, but does not lock it into one position, thus allowing the LCNC complex to function normally during gait. The orthotic device, in another embodiment, is designed and shaped to achieve a restored bone state by supporting the LCNC complex. In yet another embodiment, the orthotic device is designed and shaped for an individual subject to achieve a restored bone state by supporting the LCNC complex and/or one or more hones in the midfoot region, by a convex region on the device situated for such support.

In another embodiment, the orthotic device is contoured with a sagittal plane convexity in what is herein referred to as the "Saddle", to provide a supportive area in front of (distal to) the heel cup. The convex support structure of the Saddle functions to support the calcaneus in the sagittal plane and the cuboid bone which helps to restore congruency of the calcaneocuboid joint, and helps to support the LCNC complex along with the LCNC Dynamic Post.

Another feature of the orthotic device is the radii or radius of curvature, i.e, the amount of curvature, imposed on the orthotic material, particularly in the convex and concave regions of the device. The radius of curvature of the convex regions, and in some cases any concave regions, is selected to lend strength and support yet prevent cracking and failure of the orthotic material. The radius of curvature of the convex and concave regions of the device are specifically placed and shaped to provide dynamic support to selected foot structures, mimicking the viscoelastic properties similar to human ligaments, which restores joint congruency and allows restored foot motion to occur.

The device, in another embodiment includes one or more concave regions, for example, a heel cup in which the calcaneus rests. In a preferred embodiment, the heel cup is unique in that it is used to hold the heel (calcaneus) in the correct position in the sagittal plane so that the calcaneocuboid joint and the LCNC complex will be congruent. In contrast to prior art orthotics that have heel cups, the concave heel cup region of the present device is contoured such that movement in the frontal plane is not prevented. This heel cup is not designed to lock the subtalar joint (STJ) into a neutral position as is often done in prior art rigid or semi-rigid orthotics. Instead, the heel cup and Saddle support the restored position of the calcaneus in the sagittal plane restoring congruency to the subtalar joint and allowing it to move physiologically in the frontal plane.

From the foregoing, it is appreciated that the functional uniqueness of the orthotic device described herein provides a process of restoring bone positioning and restoring joint congruency, and to allow normal foot motion and function during gait. Orthotics known in the art prior to the device described herein were typically rigid and acted like a splint to hold the foot in a position that maintains subtalar neutral. Such orthotics do not allow normal foot motion or function to take place. Any initial pain relief is generally due to the splinting effect of painful joints by the rigid orthotic. The other broad category of orthotics, accommodative orthotics, is soft and does not support joint congruency and does not restore normal foot function. Lastly, prior art semi-rigid orthotics are no more than a compromise between a rigid orthotic that is painful during gait and a soft, accommodative orthotic that provides cushioning but lacks support. None of these prior art orthotics restore joint congruency or physiologic foot function With reference to FIG. 13C, the orthotic device is shown in side view. As seen, the trim line of the orthotic may be turned upward, as indicated by the region encompassed by arrows 150a, 150b, 150c, 150d. While many orthoses can and do have this type of trim line, the orthotic of the present application differs in that the high lateral trim line and the imposed radii, in conjunction with the device fabricated from a tensegrity-weave material acts to give the orthotic added rigidity and strength. Preferred exemplary weave material are described in U.S. Pat. No. 4,774,954 and U.S. Pat. No. 4,778,717, which are incorporated by reference herein. The composite materials are prepared from two layers of fabric material comprised of fibers of carbon, glass or aramid, where the layers can be woven threads, unidirectional fibers or random strand mats. The resulting materials are rigid, thin, and lightweight. A core of a thermoplastic material, such as an acrylic material, is included in the composite material to render the material thermoplastic. Another composite material is made of layers of woven fabric and biaxially reinforced fibers, the layers being bonded together with a thermosetting adhesive (see, U.S. Pat. No. 4,774,954). Materials for the fibers include, but are not limited to, the synthetic aramid fiber identified by the trademark Kevlar®, graphite, and e-glass.

Another exemplary foot orthotic device is illustrated in FIGS. 14A-14F. Orthotic device 170 is formed of a substrate 171 that has a proximal heel region 172, with a concave contour to accept the heel of a patient's foot. The shape and extent of the concavity in region 172 is designed, in some embodiments, to achieve congruency between the LCNC complex and the calcaneocuboid joint. A distal region 174 of the device is designed and sized for a custom shape with the terminal edge 176 of the device terminating at approximately the metatarsophalangeal joints of the foot, when the device is in contact with a foot. As seen, terminal edge 176 in this exemplary device is not a straight or gently curved edge, but undulates, as best seen in FIG. 14A and FIG. 14C, to achieve an individualized point of contact with one or more foot structures for a particular patient requiring a particular repositioning of a mid-foot bone. The undulation of edge 176, in this embodiment, provides a projection region 178, best seen in FIG. 14C, that provides contact with, and foot structure adjustment to, one or all of the second, third or fourth metatarsals and allows the first and fifth metatarsal heads to have contact with the ground thus restoring the transverse metatarsal arch. A convexity 180, best seen in FIG. 14D, is present in the projection region 178 to achieve the desired adjustment to the foot structures.

With continuing reference to FIGS. 14A-14F, device 170 also includes a convex region 182, seen best in FIG. 14F, that correspondingly engages the Saddle region of a foot, to adjust and reposition a particular midfoot structure, preferably a bone in the midfoot, to restore congruency to foot bones that are determined by the method described herein to be out of congruency. Medial side 184 of device 170 is contoured, as seen in FIGS. 14C and 14F, to engage the arch of the foot. It will be appreciated that the extent of curvature in the region of the device that contacts the foot arch can be tailored for individual patient foot shapes and needs.

It will be appreciated that the foot orthotic devices illustrated in FIGS. 13-14 are exemplary, and that the actual contour of the device will vary accordingly for particular patients. The devices as shown are in the form of an insert that can be removably placed in footwear. However, footwear designed with a non-removable or permanent sole that acts as the custom, individualized foot orthotic is contemplated. In one embodiment, the orthotic device is a unitary structure, which intends that the device is not a laminate device or is a footwear having a permanent sole that is the orthotic device. Orthotics designed in accord with the methods and systems described herein are also contemplated for use in any orthopedic device, including but not limited to casts of a lower extremity. It will also be appreciated that the methods and systems described herein can be used to design a shoe last, for manufacture of a shoe having a sole customized for a patient and that positions one or more bones in the patient's foot into a restored bone state.

It can be appreciated that the methods and systems for designing a foot orthotic, and the toot orthotic device, are not limited to any particular disease, condition, or patient complaint. However, in sonic embodiments, treatment of specific patients and/or conditions is contemplated. In one embodiment, a person suffering from diabetes mellitus and experiencing a foot ulcer is treated according to the method and system described herein. A digital anatomy of the foot is obtained, and a restored bone position is determined that will relieve pressure during walking and standing in the foot ulcer region. An orthotic device is manufactured that positions the foot bones in the restored bone position, thus alleviating pain during walking and standing, and permitting the ulcer to heal.

In another embodiment, a patient presenting with a Morton's neuroma is treated according to the method and system described herein. A digital anatomy of the foot is obtained, and a bone position is determined that will relieve pressure during walking and standing in the foot ulcer region. An orthotic device is manufactured that positions the foot bones in a restored bone position, thus alleviating pain during walking and standing, and permitting the ulcer to heal. In other embodiments, the methods, systems and orthotic device described herein are used to treat foot disorders in athletes, such as plantar fasciitis or Achilles tendonitis, to treat adult acquired flat foot syndrome, to treat gait or foot disorders associated with neurological disorders such as multiple sclerosis, muscular dystrophy, cystic fibrosis, and to improve gait in amputees.

It will be appreciated that the methods and systems described herein are not limited to design of orthotic devices, but are additionally contemplated for use more generally in evaluating bones, joint, and tissues anywhere in the body. For example, the methods and systems can be applied to the wrist or arm, for example in a patient complaining of carpel tunnel syndrome, or to the back in a person with back pain. Use of the methods and systems to obtain a digital image of any body region is contemplated, and exemplary embodiments include but are not limited to the knee, the ankle, the hip, the elbow, a finger, the shoulder, the neck, etc.

Figure 15:
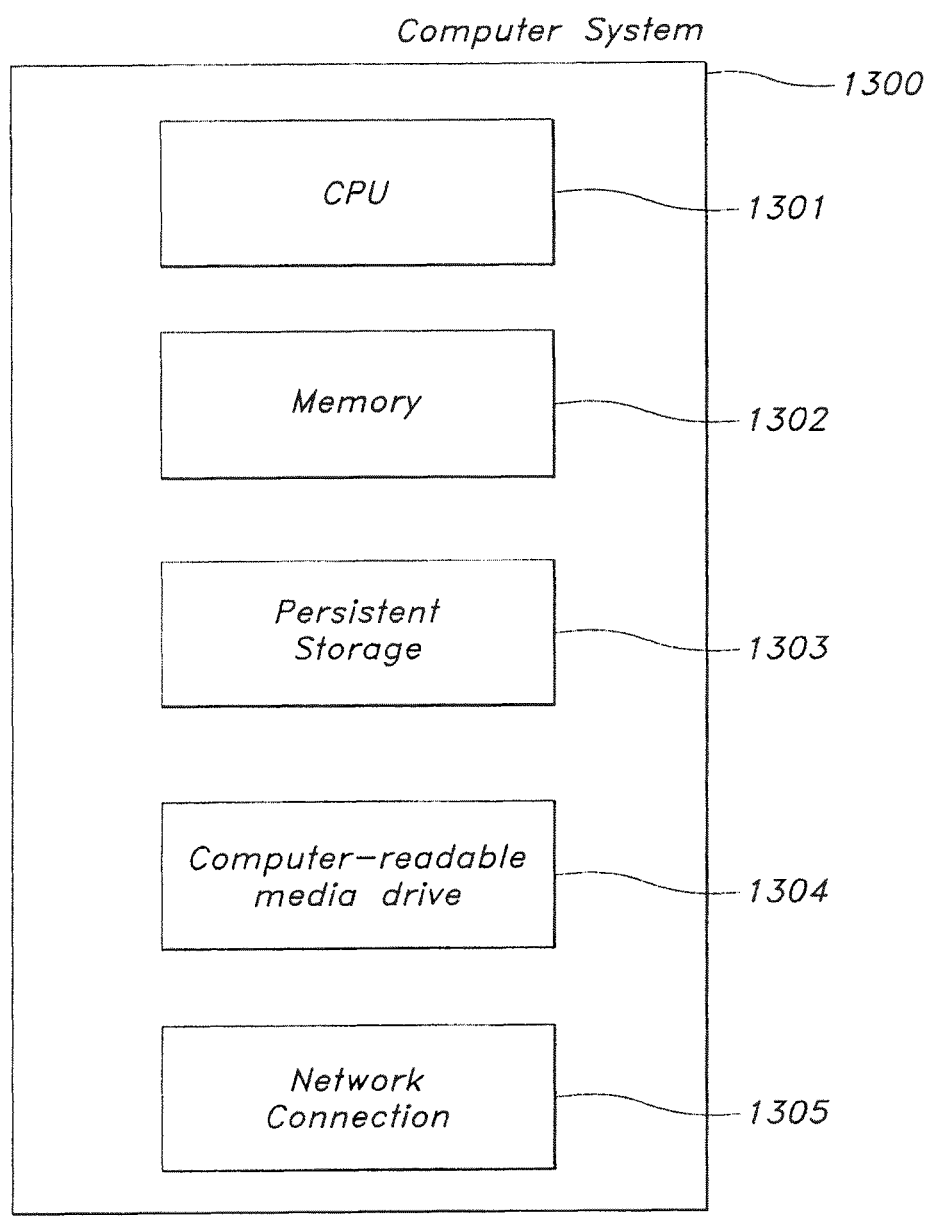
FIG. 15 is a block diagram showing some of the components typically incorporated in at least some of the computer systems and other devices performing the described methods.

FIG. 15 is a block diagram showing some of the components typically incorporated in at least some of the computer systems and other devices performing the described methods. These computer systems and devices 1300 may include one or more central processing units ("CPUs") 1301 for executing computer programs; a computer memory 1302 for storing programs and data while they are being used; a persistent storage device 1303, such as a hard drive for persistently storing programs and data; a computer-readable media drive 1304, such as a CD-ROM drive, for reading programs and data stored on a computer-readable medium; and a network connection 1305 for connecting the computer system to other computer systems, such as via the Internet. While computer systems configured as described above are typically used to support the operation of the facility, those skilled in the art will appreciate that the facility may be implemented using devices of various types and configurations, and having various components.

III. EXAMPLES

Aspects of the present teachings may be further understood in light of the following examples, which should not be construed as limiting the scope of the present teachings in any way.

Example 1

Measurement of a Patient's Foot to Obtain a Digital Anatomy

A patient experiencing pain in the left foot during physical activity is provided. The patient is seated and her bare foot is placed, under minimal weight-bearing conditions, on a foot platform having a pin bed comprised of an array of independently moveable pins. The pins within the pin bed are moved up toward the plantar surface of the foot by means of servos under control of a computer. A baseline reading of the patient's foot is acquired with the pins gently touching the plantar surface of the foot. The "ball" of the heel and first and fifth metatarsal heads ideally results in 0.0 mm pin elevation. In some embodiments, the pins are flush with the surface of the bed with the baseline reading taken when a small amount of pressure (that will not displace any soft (issue) is applied to the pins to elevate them just enough to touch the plantar surface of the foot. Pin height is displayed in small increments (0.10 to 0.05 mm) and measurement of pin elevation is used by the computer software to produce graphic representations, such as that shown in FIG. 4A, or a three-dimensional wireframe image such as that shown in FIG. 4B.

Then, a selected pressure is applied individually to each pin or groups of pins to achieve compression of the soft tissue on the plantar surface of the foot to a uniform density per pin head which is dictated by the underlying osseous structures and the thickness and density of the soft tissues. For example, even though all pins are under the same pressure, a pin that pushes into an area of the foot that has a thin covering of soft tissue over a bone will elevate a smaller amount than a pin that presses into a thick area of soft tissue that does not have underlying bone. Measurements of pin elevations under the selected pressure are used by the software to produce graphic representations of the foot. Measurements of pin elevation may be taken under multiple pressures to create a series of graphic representations.

Example 2

Analysis of a Digital Anatomy

A patient's foot is placed on a foot platform comprising a pin bed. A pressure is applied to the pins in the bed to compress the soft tissue on the plantar surface of the foot to create a uniform density of tissue per cubic centimeter at each pin head surface. The computer program collects pin height for each pin and analyzes the information to determine bone positions of the foot, first assessing the shape of the interior surface of the calcaneus. As seen in FIG. 4A, the inferior surface of the calcaneus in a healthy or restored foot is a circular shape. If the calcaneus is not in an ideal position, the shape will appear as an oval indicating that the calcaneus is plantar flexed, as visible in the contour plot of the foot in FIG. 5A. The computer then uses this data to conduct an analysis of the foot, using the following exemplary technique based on the digital image shown FIG. 6A.

The computer constructs four lines starting with an image of scanned foot, as shown in FIGS. 6B-6F:

Line 1 (Identified in FIG. 6C as Solid Line 1):

The computer software will automatically fit an oval over the part of the calcaneus closest to the ground and use its long axis to define Line 1.

Line 2 (Identified in FIG. 6D as Solid Line 2):

The computer software identifies the hourglass shape of the cuboid, as indicated in FIGS. 6B-6F, by the dashed trapezoidal shaped on the digital image corresponding to the position of the cuboid, and draws a reduction line through the middle of the proximal end of the cuboid, through the middle of the distal end of the cuboid, bisecting the proximal and distal surfaces of the cuboid. This line is identified in FIG. 6D as Line 2.

Line 3 (Identified in FIG. 6E as Solid Line 3):

The computer software draws a line in the space between the fourth and fifth metatarsals of the foot (between the fourth and fifth rays). The software will determine the locations of the bases and the heads of the fourth and fifth metatarsals, as illustrated by the region denoted by the dotted line in FIG. 6B. The computer software then draws a line between the fourth and fifth metatarsals using the two points that lie between the fourth and fifth bases and heads, respectively. This line is identified as Line 3 in FIG. 6E.

Line 4 (Identified in FIG. 6F as Solid Line 4):

The computer draws a reduction line calculated by the software from the center points of the five metatarsal heads. This line is identified in FIG. 6F as Line 4.

Figure 6A:
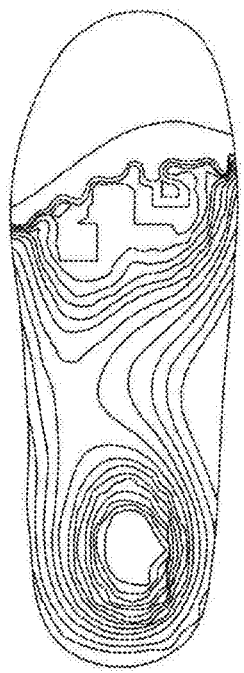
FIGS. 6A-6F are graphic illustrations of a digital anatomy of an abnormal foot, and the computer-assisted technique for analyzing the image to design a foot orthotic.
Figure 6B:
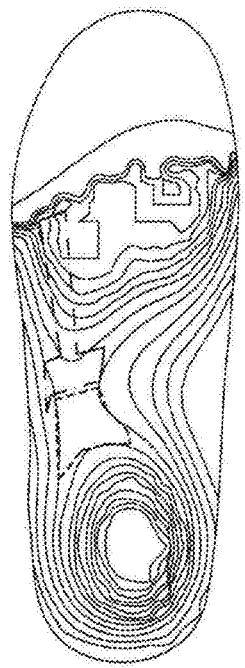
Figure 6C:
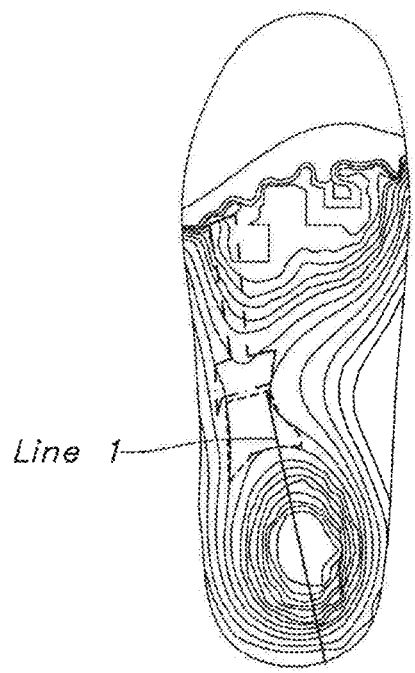
Figure 6D:
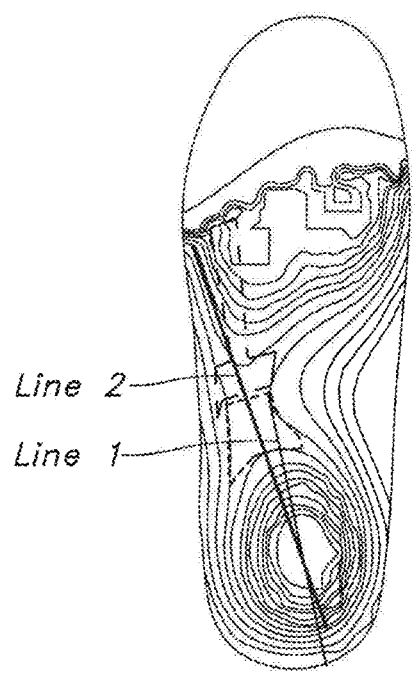
Figure 6E:
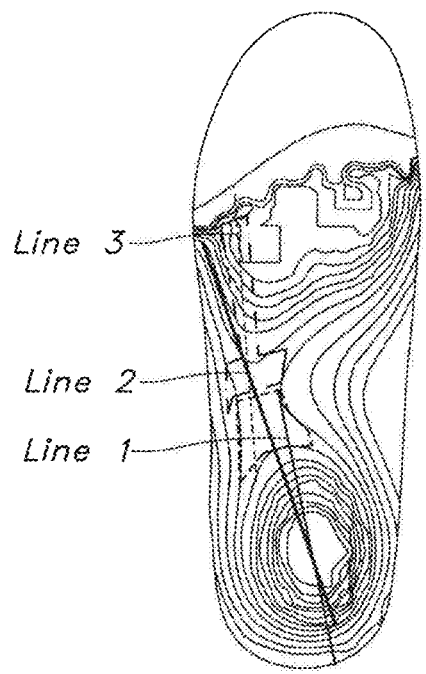
Figure 6F:
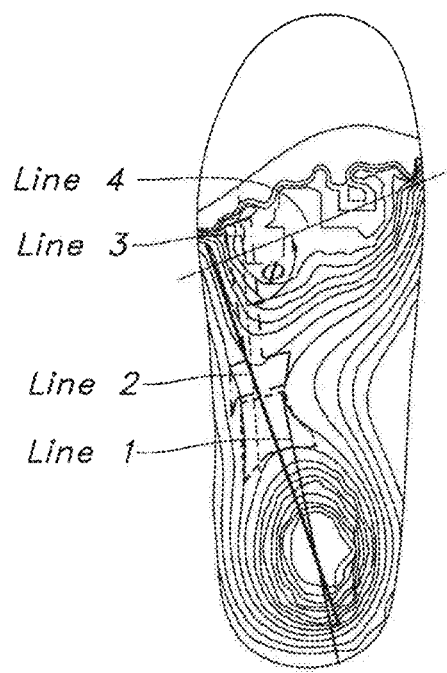

The Transverse Metatarsal Angle (TMA) is an angle created by the intersection of Lines 3 and 4, indicated in FIG. 6F as "theta", and should be 90° in the ideal physiological setting. The software uses these four lines along with pin elevation data to determine how to move the bones of the foot so that lines 1, 2 and 3 will become superimposed and so that line 4 intersects the three superimposed lines at approximately a 90° (+/−3°) angle, creating a custom simulation of the repositioning of the bones of the foot. If additional imaging is used, this data is supplemented to the pin box data.

The Heel Cup:

The computer software then measures the angles formed by the lateral and medial sides of the calcaneus as they relate to the ground. This evaluation is most clearly seen in the graphical representations shown in FIGS. 4B and 5B. The goal is for the angles created by each side of the calcaneus as it relates to the ground to be equivalent, while the lateral side of the calcaneus can only be elevated to the point where the calcaneocuboid (CC) joint remains/becomes congruent. Moving the lateral side of the calcaneus to be more perpendicular to the ground will increase the angle of the medial or lateral longitudinal arches. The increase in arch angle is usually much greater on the medial side. If this proves to be uncomfortable for the patient, the computer is programmed to incrementally decrease the elevation of the medial arch.

Example 3

Analysis of a Digital Anatomy

A digital anatomy of a foot is obtained as described in Example 1. Three series of calculations are performed by the system software to design a restorative foot orthotic device.

First, the calcaneocuboid (CC) and LCNC congruencies are calculated by drawing and evaluating several lines which transect 1) the long axis of the calcaneus footprint, 2) the axis formed from the bisection of the proximal and distal surfaces of the cuboid, 3) the space between the fourth and fifth rays (which will exhibit a deviation if the calcaneocuboid joint is dysfunctional). Additionally, a reduction line is drawn through the curve of the metatarsal heads that should bisect a line going through the lateral column in a nearly perpendicular fashion. Second, the software program defines the angle of the calcaneus and defines the heel cup. Third, the software program delineates the area under the midfoot to be supported by LCNC Dynamic Post, now to be described with reference to FIG. 12. In FIG. 12, the positioning of the LCNC Dynamic Post begins with defining a semi-circle where the calcaneal apophysis sits by identifying the upward angle of the calcaneus ending at the transverse tarsal joint where the cuboid and navicular articulate with the calcaneus. This corresponds to the area of the oval identified by arrow 120 in FIG. 12. Oval 120 seen in this figure correspondingly aligns mostly with the cuboid bone, as the rounded inferior surface of the navicular becomes part of the proximal medial longitudinal arch. The golf club head-shaped area delineated by the dotted line identified by arrow 122 is the major supportive structure of the LCNC Dynamic Post. Its apex corresponds to the metatarsal apex under the second and third metatarsals. The angles of descent and elevation in the LCNC Dynamic Post are unique to each foot, but the golf club head-shaped area mirrors the foot in an ideal, stable position. Thus, the post need not hold the weight of the body, but rather it holds the articulations of foot bones in a congruent position as the foot holds the body weight. The LCNC Dynamic Post becomes flat abruptly at the metatarsal heads, shown as the five oval solid circles in FIG. 12, designated 124a, 124b, 124e, 124d, 124e. This corresponds to the curved club-shape of the metatarsal heads (in the sagittal plane) and allows free weight distribution from one metatarsal head to the next during gait. While not wishing to be bound by any particular theory, it is believed that the larger surface area present at the first metatarsal head is likely explained by the larger diameter of the first metatarsal head and, when considered with the sesamoid bones, this diameter approximates double the diameter of the second metatarsal. This information can be displayed to the practitioner on a computer screen and/or it can be saved on digital media.

For restoration of the calcaneocuboid (CC) joint and LCNC complex congruencies, the computer calculates the bone movement needed to make Lines 1, 2 and 3 illustrated in FIGS. 6B-6F congruent and to achieve a TMA of 90°. The LCNC Dynamic Post can also be defined by the computer and an orthotic can be custom shaped to ensure the arches support themselves rather than requiring the arches to bear weight as in currently available functional orthoses. The initial base of the LCNC Dynamic Post can be determined by four points that are acquired and calculated by the system: (a) the most inferior part of the head of the first metatarsal; (b) a calculated point between the most inferior parts of the fourth and fifth metatarsal heads; and (c) the most inferior point of the lateral side of the calcaneocuboid joint. By restoring the tarsal bones positions, the foot can function in a more physiologically optimal manner, flexing and locking when required.

The apex of the LCNC Dynamic Post can be identified using pin bed data, placing the apex of the ridge at the highest point on the undersurface of the second metatarsal. This point lies about one third of the way proximal to the second metatarsal head.

The first metatarsal head along with its sesamoid bones are weight bearing structures that do not require orthotic support and must be at ground level for proper toe-off. The computer software program can subtract out this area and bring the pins down to zero elevation after the initial base of the LCNC Dynamic Post is established.

Thus, the computer can establish an outline of the final base of the LCNC Dynamic Post, wherein the outline curves proximal to the head of the first metatarsal. The three-dimensional shape of the LCNC Dynamic Post can be created by the computer connecting all the above points on the final base outline back to the apex (described above) by following the curvature of the overlying corrected bones.

For restoration of the heel cup, the computer can measure the lateral and medial calcaneal angles. If they are not roughly equivalent, the computer can vary the configuration of the LCNC Dynamic Post.

Using the methods and system described herein, the computer can analyze and evaluate trade-offs for the recommended design of a custom orthotic.

Example 4

Design of an Orthotic Device

A system can be used for design of an orthotic device, wherein the system comprises a foot-measuring and analyzing bed or platform having a plurality of individually moveable gauging elements such as pins, wherein the gauging elements are moveable when in contact with a foot placed on the bed or platform and can be moved to a desired position; and a computer program for analysis of a digital anatomy and evaluation of the relationship between two or more bones in the foot, and for determining an adjustment to one or more gauging elements of the foot-measuring and analyzing bed or platform; and, optionally, a display capable of displaying digital anatomy of the foot.

Example 5

Manufacture of an Orthotic Device

The manufacturing instrument can be a pin box, as illustrated in FIG. 11, for example. Other features of the manufacturing instrument can include: (i) pins covered by a durable, smooth and pliable material (such as a tensegrity-weave material, rubber, etc.) that will conform to the specific pin configurations from many patients, and thick enough to prevent the pin heads from pitting the finished product. The computer will compensate for this thickness; (ii) pins which can be moved into position by the computer and locked in place; and (iii) a blank insert (such as a flat sheet of the material(s) being used to fabricate the orthotic) which will be heated to a temperature (dependant on the material) to confer pliability sufficient to allow the material to be pressed into the shape of the custom orthotic. The blank insert can be positioned on top of the covered pins, the housing of the manufacturing instrument closed, and a rapidly produced, strong vacuum applied to shape the orthotic. After cooling, the orthotic is removed from the machine and the edges can be smoothed using a carbide wheel.

Example 6

Treatment Plan

Patient #1: Chief complaint: A 66 year old white male presented with bilateral foot pain for an unknown period of time which had gradually increased to a severe burning and aching pain associated with swelling, tingling and some weakness.

History of the chief complaint: Patient denied specific injury and stated the pain gradually and progressively increased over a period of months. The pain was partially relieved with stretching the foot, rest, and exercising the foot. The pain was worsened by prolonged exercise, sitting for a long period of time, prolonged walking (for example after the first few holes of a round of golf), and standing upright.

Prior treatment for the chief complaint: Patient used custom functional orthoses on both feet and arrived for evaluation wearing them in both shoes. He admitted to continued pain while wearing the orthotics.

Past medical history: High blood pressure, benign prostatic hypertrophy, renal adenoma. Past Surgical History: Bilateral inguinal hernia repairs.

Physical Exam: General appearance: Healthy, well built, and appeared to be in some discomfort. Feet: There was 1+ (on a 0 to 3+ scale) non-pitting edema to both feet with a few petechiae near the ankles, callous formation at the heel, medial to the first metatarsal head and lateral to the fifth metatarsal head. The feet were hypermobile between the rear foot and mid foot. Because of this hypermobility, his medial and lateral columns were dysfunctional and the foot was pronated. Pulses and sensation were intact bilaterally. Back: Mild lower lumbar tenderness without swelling or decreased range of motion. The remainder of the physical exam was unremarkable.

Diagnosis:
1. Plantar fasciitis
2. Hypermobility of the midfoot
3. Functional hallux limitus
4. Mild tarsal tunnel syndrome.

Clinical Course:
The patient's feet were manipulated to restore ideal congruency to the joints of the midfoot and first ray of the foot.

This was performed by raising and rotating the cuboid while also elevating the navicular and lateral cuneiform until congruency was established.

The patient was then scanned on a pin bed machine. The left foot scanned as being in ideal congruency but the right foot showed that the lateral column was still depressed. The right foot was re-manipulated using an impulse adjusting instrument. The foot was then re-scanned and showed congruency within normal limits. Both feet were taped and the patient was instructed how to do this himself at home until the orthotics could be delivered to him.

Orthotics were manufactured according to methods disclosed herein. Until the orthotics were delivered, the patient continued to tape his feet and reported excellent results including the ability to walk and play 18 holes of golf without foot discomfort for the first time in years.

Upon beginning wearing the orthoses, the patient reported continued relief of his symptoms. After three weeks of orthotic use, the patient continued to report relief of symptoms and continues to wear the orthotics daily.

Example 7

Treatment Plan

Patient #2: Chief complaint: A 46 year old white female complained of severe bilateral, aching pre-tibial area pain and mild aching foot pain.

History of the chief complaint: The patient reported the pain began in July 1991 while she was standing and walking for prolonged periods of time over consecutive days in her position as a medical resident. Secondary symptoms included moderate aching neck and upper back pain which were present since 1979 but worsened after onset of the foot symptoms. Symptoms were worsened by standing and walking. Symptoms were relieved by rest and elevation of the feet.

Prior treatment consisted of non-steroidal anti-inflammatory agents. The patient had never worn orthotics.

Past medical history and past surgical history were unremarkable.

Medications: Patient used non-steroidal anti-inflammatory agents as needed for foot or neck pain.

Physical Exam: General appearance: Healthy, well nourished, physically fit and in no distress. Legs and Feet: Both feet appeared normal with the exception of a mild callus under the third metatarsal head. There was 1+ (on a 0 to 3+ scale) pre-tibial swelling with shiny skin and mild tenderness in that area. The feet were not swollen and had normal sensation. However, pedal pulses were slightly decreased (3+ out of 4) bilaterally. The patient had bilateral medial-posterior tibial tenderness indicative of shin splints. Plantar and dorsi-flexion of both feet were uncomfortable at the extremes. Both feet showed intact medial and lateral columns but the linkage between them was partially broken down (the LCNC Complex was dysfunctional). Neck and Back: Increased lordotic and kyphotic curves to the neck and back. There was mild thoracic back tenderness. The rest of the exam was unremarkable.

Diagnosis:
1. Plantar fasciitis
2. Chronic anterior compartment syndrome
3. Pathologic gait
4. Cervical and thoracic myofascial pain Clinical Course:

Effleurage of both legs was performed followed by manipulation of both feet with the goal of improving joint mobility. Manual manipulation elevated and rotated the cuboid while also elevating the navicular and lateral cuneiform such that joint congruency was attained in the midfoot and lateral column. The feet were scanned on a pin bed machine and were found to be within normal limits.

The patient's feet were then taped and the patient was instructed how to tape them herself at home until the orthotics could be manufactured and delivered.

Orthotics were manufactured according to methods disclosed herein. After delivery of the orthotics, the patient went on a ski trip but did not use the orthotics or tape while skiing. She reported severe pain while skiing. After returning home, the patient inserted the orthotics in New Balance™ athletic shoes and reported complete relief of all symptoms within one day. After two weeks of orthotic use the patient reported continued relief.

While various embodiments have been illustrated and described by way of example, it is not intended that the present teachings be limited to such embodiments. Although specific terms are employed herein, they are used in a generic and descriptive sense only and not for purposes of limitation. Similarly, various changes can be made to the teachings without departing from the spirit and scope of the present teachings. Thus, the present teachings encompass various alternatives, modifications and equivalents, as will be appreciated by those of skill in the art.

All literature and similar materials cited in this application, including, but not limited to, patents, patent applications, articles, books, treatises, internet web pages and other publications cited in the present disclosure, regardless of the format of such literature and similar materials, are expressly incorporated by reference in their entirety for any purpose to the same extent as if each were individually indicated to be incorporated by reference. In the event that one or more of the incorporated literature and similar materials differs from or contradicts the present disclosure, including, but not limited to defined terms, term usage, described techniques, or the like, the present disclosure controls.

What is claimed is:

1. A system, comprising:
a plurality of movable elements for contact with a plantar surface of a foot, each element in said plurality capable of independent movement under control of the system for contact with a first region of the plantar surface at a first pressure and a second region of the plantar surface at a second pressure.

2. A system as in claim 1, further comprising a plurality of drivers for said movable elements, wherein said plurality of drivers are coupled to an element for movement of the element at a controlled pressure.

3. A system as in claim 2, wherein the plurality of drivers each comprise a piston driven by a pressure source.

4. A system as in claim 3, including a common pressure source which is connected to each of the pistons.

5. A system as in claim 3, including a plurality of pressure sources with at least one pressure source connected to each piston.

6. A system as in claim 2, wherein the plurality of drivers comprise a plurality of servo-controlled motor adapted to move an associated element.

7. A system as in claim 2, wherein the plurality of drivers comprise constant force springs.

8. A system as in claim 1, further comprising a plurality of sensors for determining a position of each element.

9. A system as in claim 2, further comprising a plurality of sensors for determining a position of each element.

10. A system as in claim 9, further comprising a controller connected to the drivers and sensors.

11. A system as in claim 10, further comprising a computer in communication with the controller.

12. An orthotic device designed by the system of claim 1.

13. A system, comprising:
a plurality of movable elements defining a surface for receiving a planar surface of a foot, each movable element in the plurality independently movable under control of the system for contact with the plantar surface with at least a first pressure and a second pressure, wherein at least one of the first pressure and second pressure is sufficient to displace a bone in the foot.

14. The system of claim 13, further comprising a computer in communication with one or more drivers associated with the plurality of movable elements.

15. The system of claim 14, wherein said computer comprises software capable of signaling to the one or more drivers to increase or decrease pressure applied to a movable element in the plurality of movable elements.

16. The system of claim 15, further comprising a display in communication with the computer.

17. The system of claim 15, wherein a position of each movable element in the plurality of movable elements is obtained by the computer and information regarding the position of each movable element is viewable on the display.

18. A system, comprising:
an array comprising a plurality of moveable elements, said elements moveable when in contact with a foot placed on said array, wherein at least two elements in the array are moveable independently at different pressures under control of the system to engage a plantar surface of the foot to displace a bone in the foot;
a display capable of displaying a digital anatomy of the foot; and
a computer program, for analysis of the digital anatomy and evaluation of the relationship between two or more bones in the foot, and for determining a pressure adjustment to be applied to a movable element.

19. A method performed in a computing system, comprising:
obtaining elevation data from movable elements in contact with a patient's foot when placed upon a foot bed;
converting the elevation data to a graphic image of a digital anatomy for display;
analyzing the digital anatomy for congruency of one or more joints in the patient's foot; and
based on said analyzing, determining an adjustment to a pressure to be applied to a movable element.

* * * * *